United States Patent
Levin et al.

(10) Patent No.: US 6,432,365 B1
(45) Date of Patent: Aug. 13, 2002

(54) SYSTEM AND METHOD FOR DISPENSING SOLUTION TO A MULTI-WELL CONTAINER

(75) Inventors: Robert Levin, San Diego; Rob Neeper, Lakeside; John Bridwell, San Diego, all of CA (US)

(73) Assignee: Discovery Partners International, Inc.

( * ) Notice: Subject to any disclaimer, the term of this patent is extended or adjusted under 35 U.S.C. 154(b) by 0 days.

(21) Appl. No.: 09/549,283

(22) Filed: Apr. 14, 2000

(51) Int. Cl.[7] .............................. B01L 3/00; G01N 35/02; G01N 35/10
(52) U.S. Cl. .................. 422/100; 422/68.1; 422/99; 422/102; 436/180; 141/31; 141/234; 141/236; 73/864.01; 73/864.51; 73/864.91
(58) Field of Search ............................ 422/100, 102, 422/68.1, 99; 436/180; 141/31, 234, 236; 73/864.01, 864.51, 864.91

(56) References Cited

U.S. PATENT DOCUMENTS

| | | | |
|---|---|---|---|
| 4,342,407 A | * 8/1982 | Citrin | .................. 222/485 |
| 5,045,047 A | 9/1991 | Hutchins et al. | |
| 5,217,572 A | 6/1993 | Guy et al. | |
| 5,334,130 A | 8/1994 | Glater et al. | |
| 5,472,672 A | * 12/1995 | Brennan | .................. 422/110 |
| 5,707,331 A | 1/1998 | Wells et al. | |
| 5,770,455 A | 6/1998 | Cargill et al. | |
| 5,849,598 A | * 12/1998 | Wilson et al. | .............. 422/100 |
| 5,961,923 A | 10/1999 | Nova et al. | |
| 6,264,891 B1 | * 7/2001 | Heyneker et al. | ........... 422/131 |
| 2002/0006359 A1 | * 1/2002 | Mathies et al. | ............. 422/100 |

FOREIGN PATENT DOCUMENTS

| | | |
|---|---|---|
| WO | WO97/10896 | 3/1997 |
| WO | WO98/24543 | 6/1998 |
| WO | WO99/13976 | 3/1999 |

* cited by examiner

*Primary Examiner*—Jill Warden
*Assistant Examiner*—Kathryn Bex
(74) *Attorney, Agent, or Firm*—Brown Martin Haller & McClain

(57) ABSTRACT

An automated sample-on-solid-support processing system includes a treatment solution supply subsystem which feeds solvent to a dispenser to dispense a measured amount of treatment solution to each well of a multi-well plate. The dispenser measures the solution within a fill container having a plurality of reservoir wells corresponding to the number of wells in the multi-well plate. The fill container is contained within a reservoir chamber that is filled with an excess of solution. Each reservoir well is surrounded by a plurality of bores which drains excess solution from the top of the fill container so that a precise amount of solution is left in the reservoir wells when solution is drained out of the reservoir chamber. Gas pressure is introduced into the reservoir chamber to force the solution out of the reservoir well through a bundle of tubes, with one tube per well, into the wells of the multi-well plate.

11 Claims, 15 Drawing Sheets

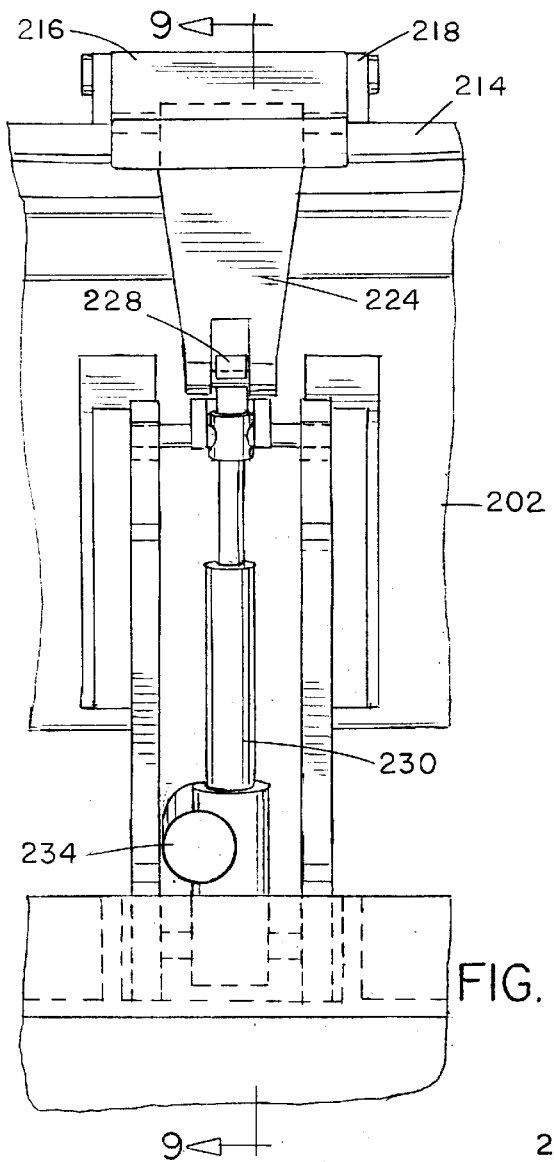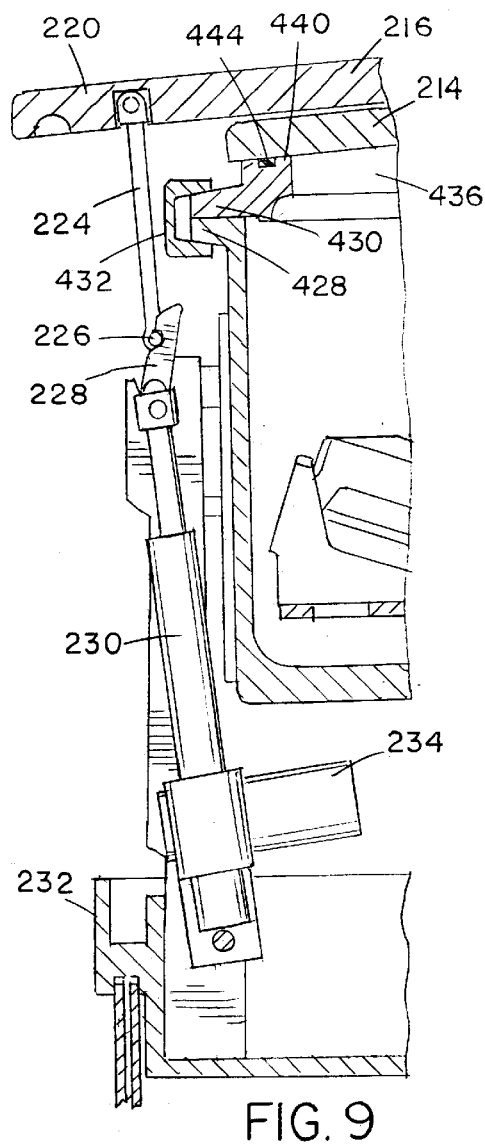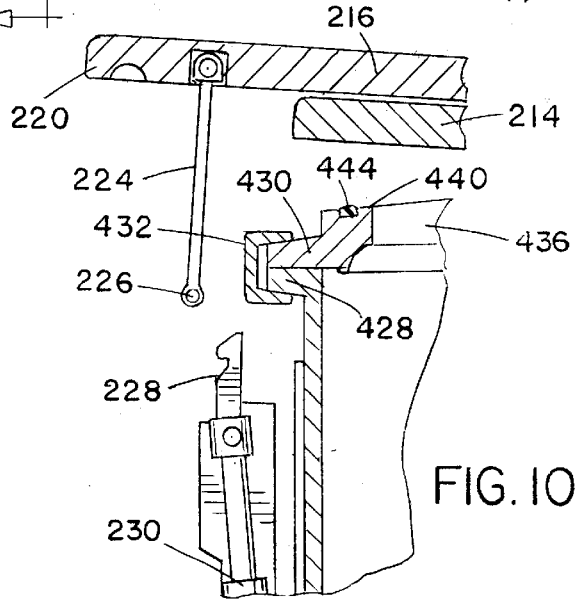
FIG. 8
FIG. 9
FIG. 10

SYSTEM AND METHOD FOR DISPENSING SOLUTION TO A MULTI-WELL CONTAINER

RELATED APPLICATIONS

This application is related to applications Ser. No. 09/549,958 entitled SYSTEM AND METHOD FOR TREATMENT OF SAMPLES ON SOLID SUPPORTS, and Ser. No. 09/549,285, entitled CONTAINER AND METHOD FOR HIGH VOLUME TREATMENT OF SAMPLES ON SOLID SUPPORTS, each having the same filing date as, and assigned to the assignee of, the present application.

FIELD OF THE INVENTION

The invention relates to a system and method for automated treatment of chemical compounds or biological materials on solid supports, and more specifically, a system and method for automated purification, elution, cleavage, transfer, concentration and/or evaporation of biological or chemical samples on solid supports.

BACKGROUND OF THE INVENTION

In recent years, the pharmaceuticals industry has devoted significant resources to finding ways to cut the time required for identification and validation of lead drug candidates. Disciplines that have arisen to address this need include high-throughput screening and combinatorial chemistry. Using combinatorial methods, libraries made up of large numbers of compounds are randomly or semi-randomly synthesized, then evaluated using high-throughput screening, looking for biological activity or chemical reactions. The availability of solid-phase supports, e.g., resin beads, balls, disks or tubes, for organic synthesis has contributed significantly to the ability to create large combinatorial libraries, making it possible to synthesize a unique compound on each support. Encoding of the solid support enables individual labeling of each compound and tracking of the compound's reaction history. Examples of tagging and tracking techniques as described in U.S. Pat. Nos. 5,770,455 and No. 5,961,923, both assigned to the assignee of the present application, the disclosures of which are incorporated herein by reference. Such tagging and/or tracking capabilities permit discrete compound split-and-pool synthesis, allowing thousands to millions of compounds to be generated at a time while keeping track of the history of each uniquely synthesized compound throughout the synthesis and subsequent cleaving operations. However, while synthesis and tracking are facilitated by solid phase methods, analysis of the compound or its intermediates may, for many tests requires removal of the synthesized compounds from their solid phase carriers, such that individualized cleavage and concentration of each compound becomes essential. Furthermore, for generation of commercial libraries, it would be preferable to provide the compounds in a convenient form that would require the purchaser to do minimal additional processing in order to perform subsequent assays or other analyses, i.e., following cleaving from the solid support and concentration of the compound. Thus, automated cleavage, concentration and collection of the compounds in a manner that significantly reduces the bottleneck in an otherwise high-throughput process, which allows the compounds to be readily tracked, and which avoids loss of material or cross-contamination between compounds, is an important step in achieving the goals of rapid drug discovery and development.

Solid phase methods have similarly been applied for analysis of biological compounds. Generally, solid phase oligonucleotide synthesis involves covalently attaching the base building block to a solid support such as controlled pore glass (CPG), polystyrene-copolymer, polyester, silica gel, polyamide/Kieselguhr,charged nylon, glass fiber, nitrocellulose or cellulose paper, then synthesizing the oligonucleotide by placing the solid support in a reaction vessel with excess protected nucleosides and coupling reagents. After completion, the oligonucleotide is cleaved from the solid support then deprotected, after which the appropriate analysis can be performed. Such methods have been adapted for purification of DNA, which typically involves the selective elution of impurities by exposing the biological sample to a number of reagents and incubating at elevated temperatures. The sample remains attached to the solid support throughout the purification steps then, if desired, the sample can be cleaved from the solid support. DNA purification procedures often require a combination of hazardous reagents, physical force (centrifuge, air pressure or vacuum), lengthy incubation periods and high temperatures (100° C.), which can require special containers and equipment that may not be well suited for very high throughput operations. For example, see International Patent Application No. WO99/13976 of Gentra Systems, Inc., which discloses an automated apparatus for isolating DNA, in which biological samples are combined with solid supports in a sample processing container, wash solution is dispensed into the containers and drained a number of times, then the sample containers are loaded onto a purification apparatus, e.g., a centrifuge. After completion of the purification step, the sample processing container is removed and moved to the next station for cleavage (elution) of the purified sample from the solid support. Thus, while the method disclosed in the referenced PCT application is automated, there is still a significant amount of handling and moving of the samples and sample containers required to complete the purification and elution process.

Systems are known for performing cleavage, elution, concentration, purification, and/or collection of multiple samples, both chemical and biological, however, such systems are not easily integrated into a single processing system that enables the handling of a large number of samples to be cleaved, concentrated and collected automatically. For example, the centrifugal system for vacuum concentration of biological specimens disclosed in U.S. Pat. No. 5,334,130 enables treatment of multiple biological samples within the centrifuge chamber. Cleavage of the compounds from their supports is effected by pouring a typically caustic cleaving agent into each vial before placing the vials into the centrifuge chamber. The chamber is sealed and heated to accelerate cleavage. After cleavage is complete, the concentration step occurs during which the chamber is evacuated and the centrifuge rotor is activated to evaporate the cleaving agent. The rotor speed can sometimes be selected to minimize "bumping" which can cause solid or liquid form material to be propelled out of the vial due to violent outgassing caused by boiling of the solvent. In the system disclosed in the '130 patent, the rotor has a number of holder positions, each of which includes a pressure relief valve for its corresponding vial, thus limiting the number of sample-containers, and consequently, the number of samples, to the number of holder position.

An important aspect of streamlining the process for synthesis, cleavage and concentration of compounds involves establishing a system that allows the compounds to be processed through multiple process steps without frequent transfer of the solid supports and/or compounds from one container to another as needed to allow a certain piece of equipment to be used. However, in the described systems, unless prior processing steps were also performed in the sample containers, transfer into such containers would be required before the cleavage and concentration procedure could be performed. Thus, the cleavage/concentration steps would become rate-limiting in a high-throughput process for several reasons which include: (1) additional handling of the samples is required to place them in the containers; (2) the often-hazardous cleavage agent must be introduced into the container, then the container carefully carried to the centrifuge chamber for loading; and (3) the cleavage and concentration steps are performed as separate procedures.

For the reasons described above, there remains a need for a system for processing of samples on solid supports, which may include cleavage, transfer/collection and/or concentration, that allows for a highly automated method of reagent delivery, cleaving, transfer and/or concentration of a large number of chemical or biological samples in a rapid, cost effective manner.

SUMMARY OF THE INVENTION

It is an advantage of the present invention to provide a system that automatically dispenses one or more liquid solutions within a centrifuge for simultaneous treatment of a number of chemical or biological samples on solid supports.

It is another advantage of the present invention to provide a system and method for automatically sample washing, eluting, cleaving, concentrating and collecting a large number of samples on solid supports.

Still another advantage of the present invention is to permit treatment of chemical or biological samples in a sealed system which avoids the need for operator handling of hazardous solutions and permits a vacuum to be applied during processing.

It is a further advantage of the present invention to provide an automated system and method for processing of chemical or biological samples that allows the processing temperature to be accurately controlled to prevent heat damage to samples and containers.

Another advantage of the present invention is to provide an automated system that significantly minimizes the possibility of cross-contamination and/or loss of samples during processing.

Yet another advantage of the present invention is to provide an automated system that precisely measures and dispenses hazardous solutions during all processing operations in a sealed system.

In an exemplary embodiment, the automated processing system of the present invention comprises a computer-based control unit and a main unit comprising a variable-speed centrifuge having an openable vacuum-tight chamber and a centrifuge rotor with a plurality of multi-sample holding positions, a liquid solution supply subsystem which feeds solvent or other solution to a plurality of dispensing stations in the centrifuge chamber, a temperature control subsystem, and a vacuum subsystem. In the preferred embodiment bar code reader or other identification means, preferably a non-contact reader, can be included in the chamber to allow sample carriers to be identified.

Solid support-bound sample compounds are retained within a multi-well sample container which is mated on its lower end with a collection container possessing a collection well corresponding to each well of the sample container. When mated, the two containers are inserted into one of the multi-sample holding positions on the centrifuge rotor. After closing the centrifuge chamber, cleaving solvent (or other appropriate reagent) is automatically dispensed into each well of the sample container, with the centrifuge rotor being rotated to position each sample container at the dispensing station. By running the rotor at a low rotational speed while dispensing and during cleavage, potential carryover of solvent and/or samples ("creep") between the wells is significantly minimized. As the rotor turns, samples are allowed to incubate until the samples are cleaved from the solid supports. When cleaving is complete as pre-programmed based upon the sample types and, for chemical compounds, the linker types, the rotor speed is increased, causing the cleaved sample and solvent to be transferred to the collection container, leaving the solid support in the sample container. After all of the cleaved solutions are transferred into the collection containers, the rotor speed is increased to a relatively high rate. The collection containers are uniformly heated, causing the cleaving solvent to uniformly evaporate at a user-programmable rate. The vacuum within the chamber is controlled to accelerate the evaporation. After a pre-determined period of time, the process is terminated, leaving the concentrated samples in the bottoms of the wells of the collection containers.

In the preferred embodiment, the control unit comprises a PC with a Windows®-type operating system to provide a user-interface via mouse or keyboard. The PC includes a memory within which is stored software for controlling and monitoring the various subsystems within the cleavage/evaporation system. Where the cleavage/evaporation system is part of a processing system for synthesizing compounds, the memory will also preferably have stored therein software for management of the synthesis, including tracking of the encoded solid supports, the chemical building blocks used in the synthesis, and the concentrated sample compounds after cleavage. The control unit also includes power supplies, the main control relay, and a network bus controller. The power supplies provide power to the main unit and any operating device within the system that requires power for operation. The control unit includes a single connection to the main electrical supply, i.e., electrical outlet, thus providing for total system control through the control unit, allowing rapid shutdown of an individual subsystem, or the entire system, if required. The main switching unit provides switching of the devices of the main unit in response to commands issued by the PC according to the control software. The network bus controller provides data transfer (I/O) between the PC and the main unit for conveying control commands to the various devices and for receiving monitoring data from the system sensors. A conventional cable provides physical connection between the control unit and the main unit.

The centrifuge chamber must be sufficiently sealed so that it is capable of maintaining a vacuum and is resistant to the harsh chemicals used during processing of the samples. In the preferred embodiment, sample-holder positions are fixed on the centrifuge rotor, with a plurality of inwardly-sloping support frames or blocks radially mounted at evenly-spaced positions around the rotor. In an alternate embodiment, the sample holders are pivotally mounted to swing at an increasing angle as the rotor speed increased. Each support frame is adapted to receive the assembled combination of the sample container and collection container. The rotor has openings therethrough at locations corresponding to each support frame to permit heating of the collection container from below the rotor. The centrifuge chamber has a plurality of heat-transmissive windows formed in its bottom side. At least one light-transmissive window is formed in the side of the centrifuge chamber to provide access for optical reading of bar codes on the sample and collection containers. A second light-transmissive window may be formed in the top of the centrifuge chamber to permit optical transmission of a signal from a temperature sensor located inside the chamber.

The solvent supply subsystem includes at least one source container and pump which provide solvent to a dispensing station. In the preferred embodiment, two dispensing stations are included, each having its own source container and pump, so that two different solvents can be supplied.

The dispensing station includes a dispensing head which is mounted on and extends into the centrifuge chamber in a manner which provides access to all wells in the sample container. The dispensing head has one dispensing tip or nipple corresponding to each well in the sample container and is arranged such that alignment of the dispensing head with the sample container causes each dispensing nipple to align with its corresponding well. Each dispensing tip is connected by a tube to a corresponding solvent reservoir in the dispenser housing. The solvent reservoir contains a premeasured amount of solvent so that the precise amount of solvent used is known. The source supply subsystem also includes a waste reservoir for safe storage of used solvent and a gas source for purging the dispenser tubing and dispensing tip.

The temperature control subsystem includes temperature sensors and heating means. Heat to the samples is supplied via infrared heat lamps positioned outside of the bottom of the centrifuge chamber at the heat-transmissive windows. Conduction and uniform dispersion of the heat entering the windows is provided by heat-conducting plates disposed within the support frames on the rotor, beneath each of the collection containers. A thermal sensor in contact with one of the heat-conducting plates provides a signal to an optical (IR) transmitter located below the light-transmissive window in the top of the centrifuge chamber. The infrared signal is detected by a detector positioned outside of the light-transmissive window and a signal is generated to provide feedback to the sample heat controller for controlling the heat lamps. Additional heat to the chamber is provided by resistive heaters mounted on the centrifuge housing, preferably on both the top and bottom of the chamber. A sensor mounted on the outside of the chamber provides feedback for controlling the chamber temperature.

The vacuum subsystem includes a vacuum controller for controlling a pair of pumps, which in the preferred embodiment are a Roots pump and a diaphragm pump. A condenser may be included for removal of vaporized solvent from the evacuated air from the centrifuge chamber to prevent possible release of the solvent into the environment.

Tracking of the location of the sample compounds is enabled by identification of the sample and collection containers. In the preferred embodiment, each of the containers is marked with an optically-readable bar code. Orientation keys are included on the containers to ensure that the bar code is visible through the window in the side of the centrifuge chamber. The bar code reader reads the encoded identification and provides that information to the control unit (PC) which stores the information in association with the synthesis histories of the samples as provided by the synthesis management software. The samples in the sample and collection containers are tracked spatially, according to the coordinates of the wells in which they are placed. As an alternative to the optical bar code, radio frequency (RF), or other remotely-readable tags may be embedded in the containers to provide means for identifying and tracking the containers.

BRIEF DESCRIPTION OF THE DRAWINGS

Understanding of the present invention will be facilitated by consideration of the following detailed description of a preferred embodiment of the present invention taken in conjunction with the accompanying drawings, in which like numerals refer to like parts and in which:

FIG. 8 is an enlarged front view of the cover latching mechanism;

FIG. 9 is a sectional view taken along line 9—9 of FIG. 8;

FIG. 10 is similar to a portion of FIG. 9, showing the cover unlatched;

DETAILED DESCRIPTION OF THE PREFERRED EMBODIMENTS

Figure 1:
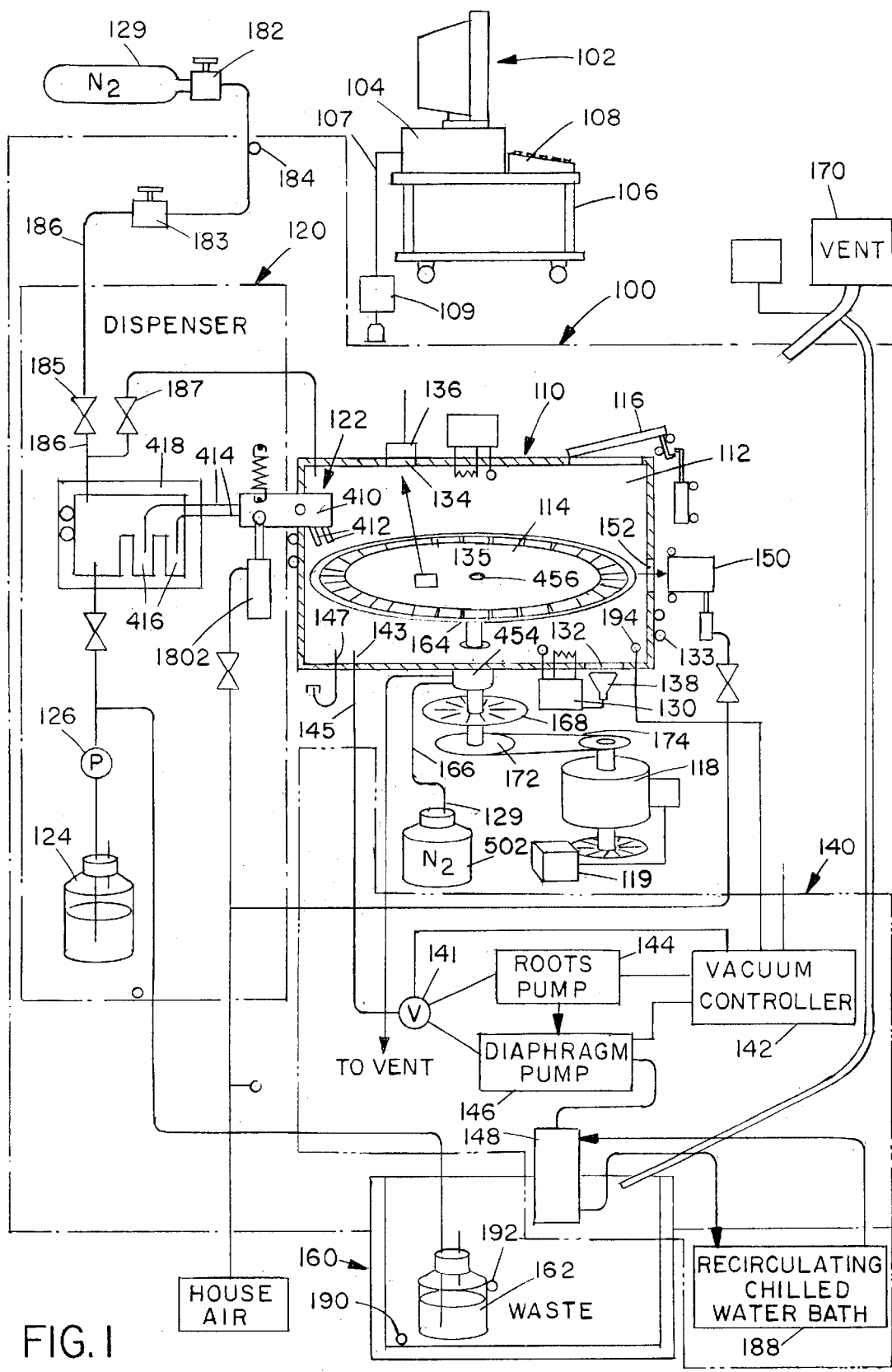
FIG. 1 is a schematic diagram of the cleavage/evaporation system of the present invention.

As illustrated in FIG. 1, the automated cleavage/evaporation system of the present invention comprises number of electromechanical subsystems and mechanical structures including: a computer-based control unit 102 and a main unit 104 containing a centrifuge 110 having an openable vacuum-tight chamber 112 and a centrifuge rotor 114 with a plurality of multi-sample holding positions, a supply subsystem 120, which includes a plurality of dispensing stations 122 (only one is shown) in the centrifuge chamber 112, a heating/temperature control subsystem 130, a vacuum subsystem 140, a bar code reader 150, waste disposal system 160, and vapor venting system 170.

For purposes of the following detailed description, the invention will be described as used for processing, i.e., cleavage/concentration, of synthesized chemical compounds. Adaptation of the inventive system for use in processing of biological samples, such as DNA purification, will be readily apparent to those of skill in the art in view of the detailed description.

The resin-bound sample compounds are retained within a multi-well sample compound container (shown in FIGS. 17 and 20–22) which is mated at its lower end with a collection container (shown in FIGS. 23 and 24) possessing a collection well corresponding to each well of the compound container. In the preferred embodiment, the sample and collection containers are 96-well plates, generally corresponding to standard 96-well microtiter plates, however, other container arrangements and well configurations can be used. When mated, the two containers are inserted into one of the multi-sample holding positions on the centrifuge rotor 114. After closing the centrifuge chamber 112, cleaving solvent is automatically dispensed into each well of the compound container, with the centrifuge rotor 114 being rotated to position each compound container at the dispensing station 122.

By running the rotor at a low rotational speed, e.g., at around 20–30r.p.m., while dispensing and during cleavage, potential carryover of solvent and/or compounds ("creep") between the wells is minimized. As the rotor turns, samples are allowed to incubate until the compounds are cleaved from the solid supports. When cleaving is complete, as determined based upon the compound and linker types, the rotor speed is increased, causing the cleaved compound and solvent to be transferred to the collection container 406, leaving the solid support in the compound container. After all of the cleaved solutions are transferred into the collection containers, the rotor speed is increased. The collection containers are uniformly heated using adaptive heating subsystem 130, causing the cleaving solvent to evaporate uniformly.

The vacuum subsystem 140 maintains a vacuum within the chamber to accelerate the cleavage and concentration of the samples. After a pre-determined period of time, the process is terminated, leaving the concentrated sample compounds in the bottoms of the wells of the collection containers.

In the preferred embodiment, the control unit comprises a PC 104 with a conventional operating system to provide a user-interface via mouse or keyboard 108. The PC 104 includes a memory within which is stored software for controlling and monitoring the various subsystems within the cleavage/evaporation system. Where the cleavage/evaporation system is part of a processing system for synthesizing compounds, the memory will also preferably have stored therein software for management of the synthesis, including tracking of the encoded solid supports, the chemical building blocks used in the synthesis, and the concentrated sample compounds after cleavage. Control unit 102 also includes power supplies, the main control relay, and a network bus controller. The power supplies provide power to the main unit and any operating device within the system that requires power for operation. Control unit 102 preferably includes a single connection to the main electrical supply, i.e., electrical outlet, thus providing for total system control through the control unit, allowing rapid shutdown of an individual subsystem, or the entire system, if required. The main control relay provides switching of the devices of the main unit in response to commands issued by the PC 104 according to the control software. The network bus controller provides data transfer (I/O) between the PC 104 and the main unit 100 for conveying control commands to the various devices and for receiving monitoring data from the system sensors. An umbilical cable 107 provides physical connection between the control unit and the main unit. Control unit 102 can be mounted on a computer cart 106 or other appropriate frame to facilitate operation and maintenance.

Figure 4:
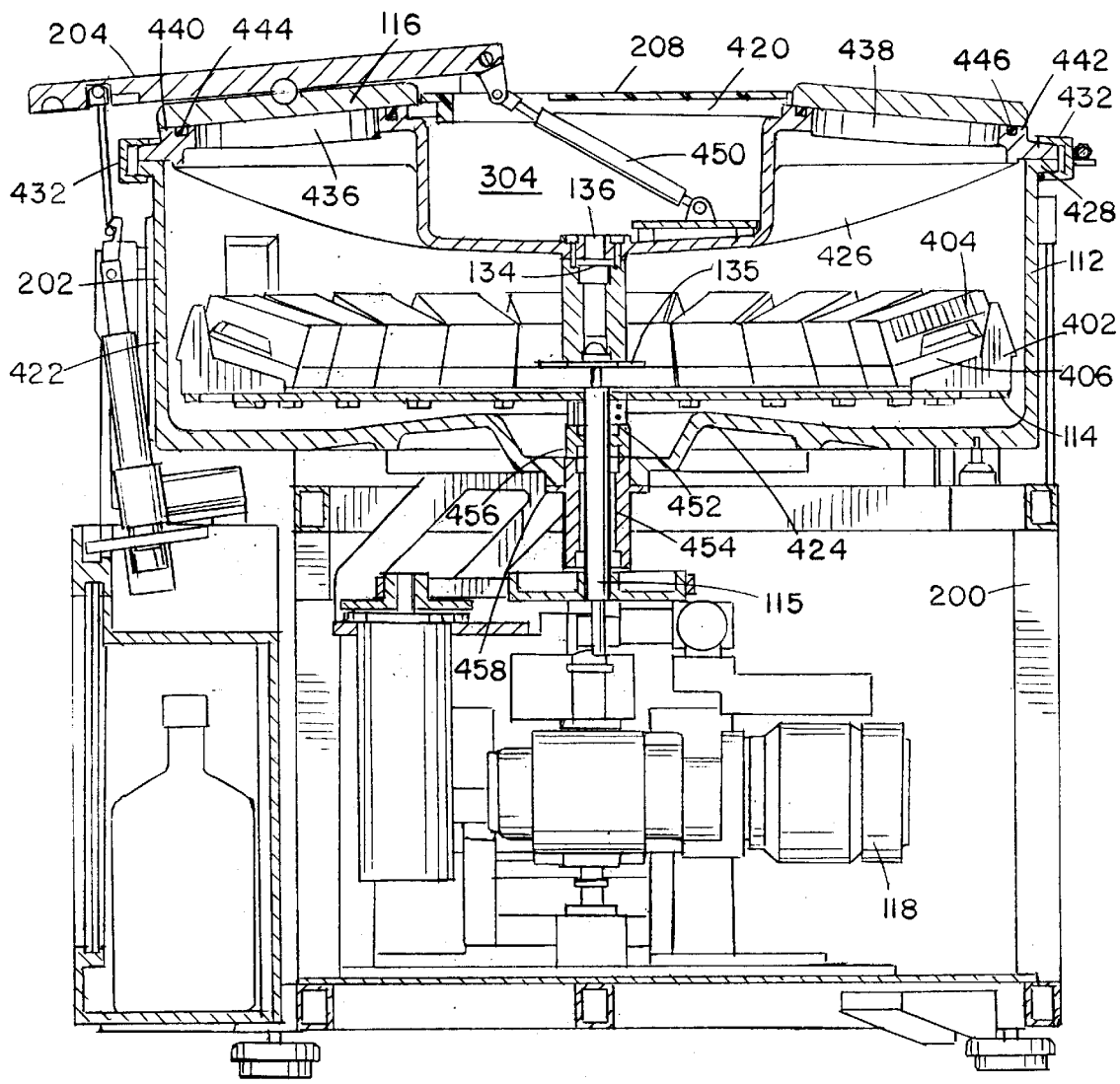
FIG. 4 is a sectional view taken along line 4—4 of FIG. 3.
Figure 7:
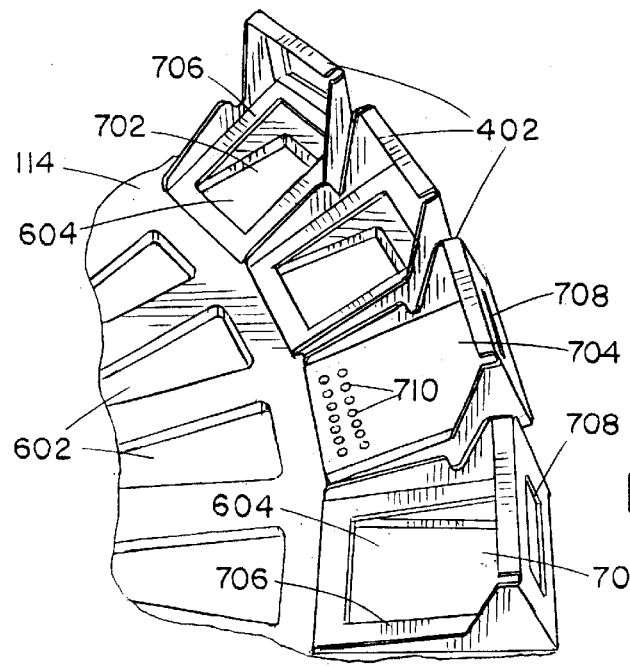
FIG. 7 is a perspective view of a portion of the centrifuge rotor showing the container holders.

Centrifuge chamber 112 must be sufficiently sealed so that it is capable of maintaining a vacuum and resistant to the harsh chemicals used during processing of the samples. Chamber lid 116 provides access to the interior of chamber 112 for loading and unloading of the sample and collection containers. In the preferred embodiment, centrifuge rotor 114 is fixed, with a plurality of inwardly-sloping support frames 402 or blocks mounted at evenly-spaced positions around the circumference of the rotor, as illustrated in FIG. 4. Each support frame 402 is adapted to receive the assembled combination of the sample container 404 and collection container 406. The rotor 114 has openings 702 therethrough at locations corresponding to each support frame to permit heating of the collection container from below the rotor, as shown in FIG. 7. Referring again to FIG. 1, centrifuge chamber 112 has a plurality of heat-transmissive windows 132 formed in its bottom side. At least one light-transmissive window 152 is formed in the side of centrifuge chamber 112 to provide access for optical reading of bar codes on the sample and collection containers. A second light-transmissive window 134 may be formed in the top of centrifuge chamber 112 to permit optical transmission of a signal from a thermal sensor 1102 located inside the chamber.

The solvent supply subsystem 120 includes at least one source container 124 and pump 126 which provide solvent to dispensing station 122. In the preferred embodiment, two dispensing stations 122 are included, each having its own source container 124 and pump 126, so that two different solvents can be supplied. Dispensing station 122 includes a dispensing head 410 which is mounted on and extends into centrifuge chamber 112 in a manner which provides access to all wells in the sample containers. The dispensing head 410 has one dispensing nipple or tip 412 corresponding to each well in the sample container 404 and is arranged such that alignment of the dispensing head 410 with the sample container 404 causes each dispensing tip 412 to align with its corresponding well. Each dispensing tip 412 is connected by a tube 414 to a corresponding solvent reservoir 416 in the dispenser housing 418. The dispensing tip 412 may actually be the end of the tube 414 itself, where end of the tube is inserted through bores in the dispensing head to define tip 412, as described below in more detail. Each solvent reservoir 416 contains a pre-measured amount of solvent so that the precise amount of solvent used is known. The source supply subsystem 120 is connected to waste collection system 160 which includes waste reservoir 162 for safe storage of used solvent and to a gas source 129 for purging the dispenser tubing and tips.

Figure 11:
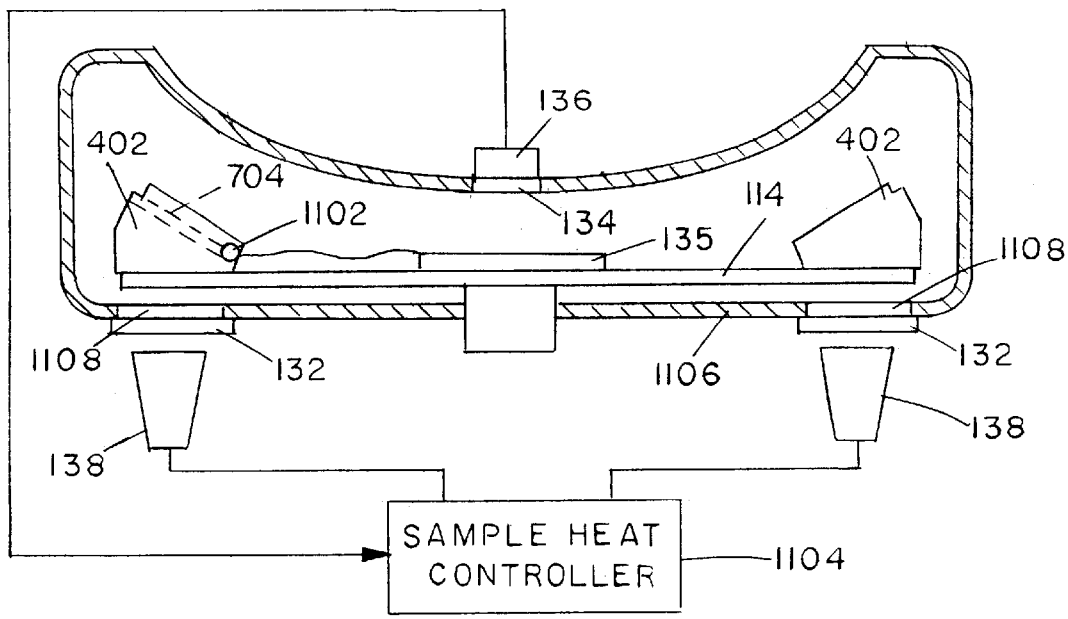
FIG. 11 is a diagram of the container heating system.
Figure 12:
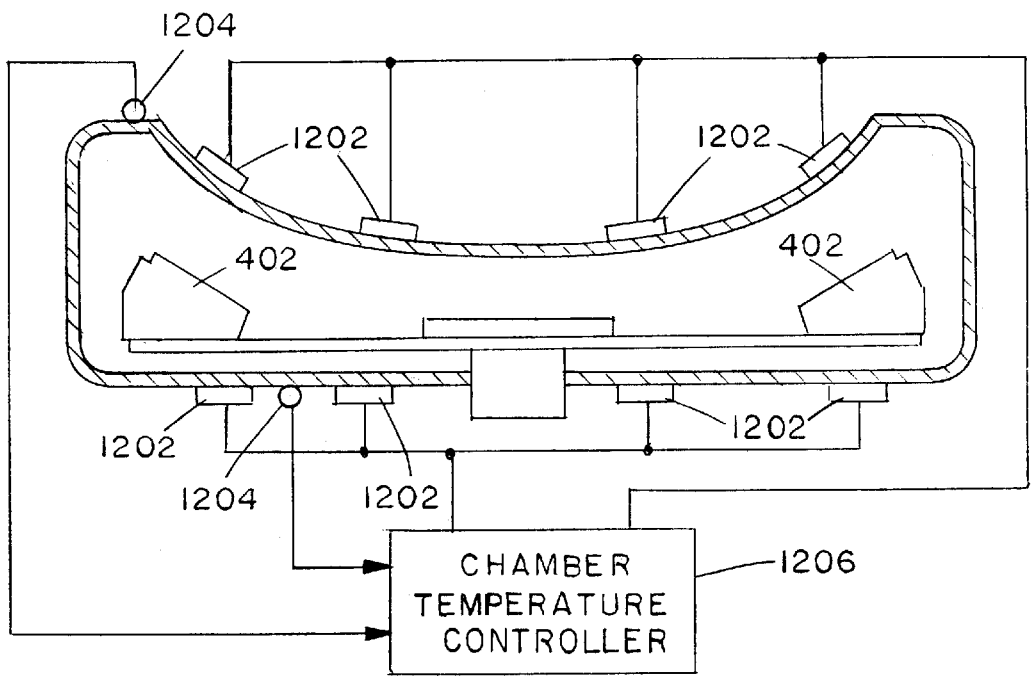
FIG. 12 is a diagram of the chamber heating subsystem.

Temperature control subsystem 130 includes temperature sensors and heating means. Heat to the samples is supplied via infrared heat lamps 138 positioned outside of the bottom of centrifuge chamber 112 at the heat-transmissive windows 132. Conduction and uniform dispersion of the heat entering the windows is provided by heat-conducting plates 704 disposed within support frames 402 on the rotor, beneath each of the collection containers. (See FIG. 7.) As shown in FIG. 11, thermal sensor 1102, which is attached to support frame 402 and in contact with one of the heat-conducting plates, provides a signal to an optical (IR) transmitter 135 located below the light-transmissive window 134 in the top of centrifuge chamber 112. The infrared signal is detected by detector 136 positioned outside of light-transmissive window 134 and a signal is generated to provide feedback to the sample heat controller 1104, and control unit 102, for adaptively controlling the heat lamps 138 so as to prevent overshoot of the temperature at the heat plates. Additional heat to the chamber is provided by resistive heaters 1202 mounted on the centrifuge housing, preferably on both the top and bottom of the chamber, as shown in FIG. 12. One or more sensors 1204 mounted on the outside of the chamber provides feedback to the chamber temperature controller 1206 for controlling the chamber temperature.

Referring again to FIG. 1, vacuum subsystem 140 includes a vacuum controller 142 for controlling a pair of pumps, which in the preferred embodiment are a Roots blower-type pump 144 and a diaphragm pump 146.

A chilled water condenser 148 may be included in-line with diaphragm pump 146 to remove vaporized solvent from the evacuated air from the centrifuge chamber to prevent possible release of the solvent into the atmosphere.

Vapor venting subsystem 170 is connected to and driven by the user's laboratory exhaust vent and draws vapor from the cabinet containing the source container 124, the area under centrifuge 110, the area around the centrifuge access door 116, and the cabinet housing the waste container 162.

Tracking of the location of the sample compounds is enabled by identification of the sample and collection containers using the identification subsystem. In the preferred embodiment, each of the containers is marked with an optically-readable bar code. Orientation keys are included on the containers to ensure that they are positioned on the rotor so that the bar code is visible through window 152 in the side of the centrifuge chamber 112. The bar code reader 150 reads the encoded identification on each container and provides the identification information to the control unit 102 (PC 104) which stores the information in association with the synthesis histories of the compounds as provided by the synthesis management software. The identities of the compounds in the sample and collection containers are tracked spatially, according to the coordinates of the wells in which they are placed. As an alternative to the optical bar code, radio frequency (RF), or other remotely-readable tags may be partially or completely embedded in or attached to a surface of the containers to provide means for identifying and tracking the containers. For example, RF tags (transponders) would be embedded in the containers at a location that faces radially outward when the containers are placed in the loading positions of the centrifuge rotor. The bar code reader would then be replaced with a scanner that is an RF transmitter/receiver which transmits an inquiry signal to the RF tag and reads the response containing data indicative of the container identity.

The following discussions provide additional details of the structure and operation of each unit and key subsystems and components within the cleavage/evaporation system of the present invention:

Control Unit 102:

Control unit 102 monitors and controls all operations and equipment devices of the cleavage/evaporation system. The control unit 102, shown in FIG. 1, comprises a control unit rack 106, a control computer, which, in the preferred embodiment is a PC 104, a user interface 108, and a control network 109. Control network 109 is illustrated in FIG. 1 as a wire-based system, connected to the main unit 100 via an umbilical 107. However, communication can also be provided by a wireless system, using RF, optical, or other transmitted signals for communication. Control unit rack 106 can be a conventional electronic equipment or computer rack with one or more shelves to support equipment. The control unit rack 106 will preferably be mounted on wheels to facilitate mobility in operation and maintenance of the cleavage/evaporation system.

PC 104 provides the primary functions of monitoring and controlling operations of the different components of the cleavage/evaporation system according to instructions generated by control network software which are communicated via control network 109.

The software which controls the operation of the cleavage/evaporation system includes an operating system, such as WindowsNT® or Windows® type systems, and control network software which is adapted to interface with or work off of the operating system. The control network software can be any software that interfaces with the control network and provides communication between PC 104 and the main unit 100, allowing PC 104 to monitor and control devices attached to the control network. In the preferred embodiment, Visual Basic™ software is used to control the system through a DeviceNet™ interface card installed in PC 104. Appropriate interface cards are widely available from a number of manufacturers of electronics for automation systems. National Instruments is one source of such interface cards.

Generally, control network 109 is a CAN (Controller Area Network), a widely-used protocol for automation applications. CAN is a broadcast-oriented, communications protocol which defines the means by which data transmission occurs, providing fast response and high reliability. In the preferred embodiment, control network 109 comprises a fieldbus system operating using the DeviceNet™ communication link and a plurality of I/O (input/output) modules which are connected to and communicate with the devices in the main unit 100. A fieldbus, which is generally known in the art, is an all-digital, serial, two-way communications system that interconnects measurement and control equipment such as sensors, actuators and controllers. The fieldbus serves a function similar to that of a Local Area Network (LAN) for instruments used in process control, remote I/O and manufacturing automation applications and has a built-in capability to distribute the control application across the network.

The DeviceNet™ communication link, which is based on the CAN protocol, describes the application layer. The DeviceNet™ protocol is object oriented. The DeviceNet™ specification is available from Open DeviceNet Vendor Association, Inc. (ODVA). Implementation of the DeviceNet™ link can be achieved using I/O devices such as the WAGO I/O System, available from WAGO® Corporation (Germantown, WI), to construct a plurality of fieldbus nodes, each comprising a fieldbus coupler, a number of special function modules, or control adapters, and a termination module. Other sources of appropriate components and systems for implementing the DeviceNet™ link include Allen Bradley I/O from Rockwell Automation and SST from Woodhead Connectivity (Waterloo, Ontario, Canada).

Under DeviceNet™, each network node is identified by a Media Access Identifier (MAC ID), which range in value from 0 to 63. Each network node can connect a plurality of network devices to the network. The control adapters allocate a unique I/O (input/output) address or object address to each separate device in the main unit, thus permitting direct access to each device.

Each signal name describes the state or process that will be true or active when that signal is true as perceived by the PC's control program. the relationship between the logical polarity (true/false state) of a signal and the voltage and current in an associated wire is as follows:

Outputs are similarly arranged in that an output signal is made "true" by the control program in the PC when the output circuit is connected to ground. A "false" output signal generated by the control program will result in an open circuit at the output terminal. For example, if a solenoid has one wire connected to +24V and the other to the output terminal, when the control program sends a "true" signal, current will flow through the solenoid so that the solenoid is activated.

Alternatively or in addition to the DeviceNet™ network, a programmable logic controller (PLC) may be included as part of control network 109 to provide an interface between the control computer and the controlled devices, e.g., to generate drive signals to activate solenoids, relays and switches required to operate the devices. PLCs are well known and widely used. Selection of an appropriate PLC and the logic for supporting its operation will be apparent to those of skill in the art.

In the preferred embodiment, software stored within PC 104 also includes programming for directing compound synthesis and handling of the solid supports and the compounds synthesized thereon. Using such software, PC 104 is capable of tracking each of the synthesized compounds from start to finish, making a record of the synthesis history and ultimate destination of the synthesized compounds. An example of such software is SYNTHESIS MANAGER™, which is commercially available from IRORI (San Diego, Calif.). A description of key components of this software is provided in co-pending application Ser. No. 08/958,254, filed Oct. 7, 1997, incorporated herein by reference, which application is assigned to the assignee of the present application.

To provide a brief description of operation of exemplary synthesis management software, in the first step of a process for building a combinatorial library, the individual building blocks, i.e., monomers, nucleotides or amino acids or other small molecules, and the steps in which they are to be used are defined. The software performs operations for automatically creating a data base record within the PC's memory for each compound to be synthesized. Pre-reaction procedures, reaction conditions, and work-up procedures are also stored for each step. The user selects the synthesis procedure and the synthesis management software generates a display of the procedure for review by the user, then reads each of the memories associated with each solid support and sorts them for the next reaction step. When the sorting is complete, the reaction condition information and work-up procedure can be displayed to the user.

When the synthesis is complete, the solid supports and their attached synthesized compounds are washed, then transferred into a multi-well sample container, such as a 96-well plate, preferably using an automated loader which is in communication with PC 104. During loading, the automated loader provides a record of the location of the well in the plate into which each compound is loaded which is stored in the database containing the synthesis history for that compound. Typically, the record will consist of a pair of coordinates, i.e., x,y coordinates, to uniquely identify each well in the plate.

After loading the sample and collection containers, the synthesis management software directs the cleavage/evaporation system to cleave the compounds from the solid supports and concentrate the compounds in the collection containers. The bar code reader of the cleavage/evaporation system provides input for creating a record linking the sample container with its associated collection container. Thus, the compounds are tracked to their final destination in the collection container. The compounds can then be stored in the collection containers with the software having created an archive consisting of the entire history of the compound found in any given well of the collection container.

Figure 2:
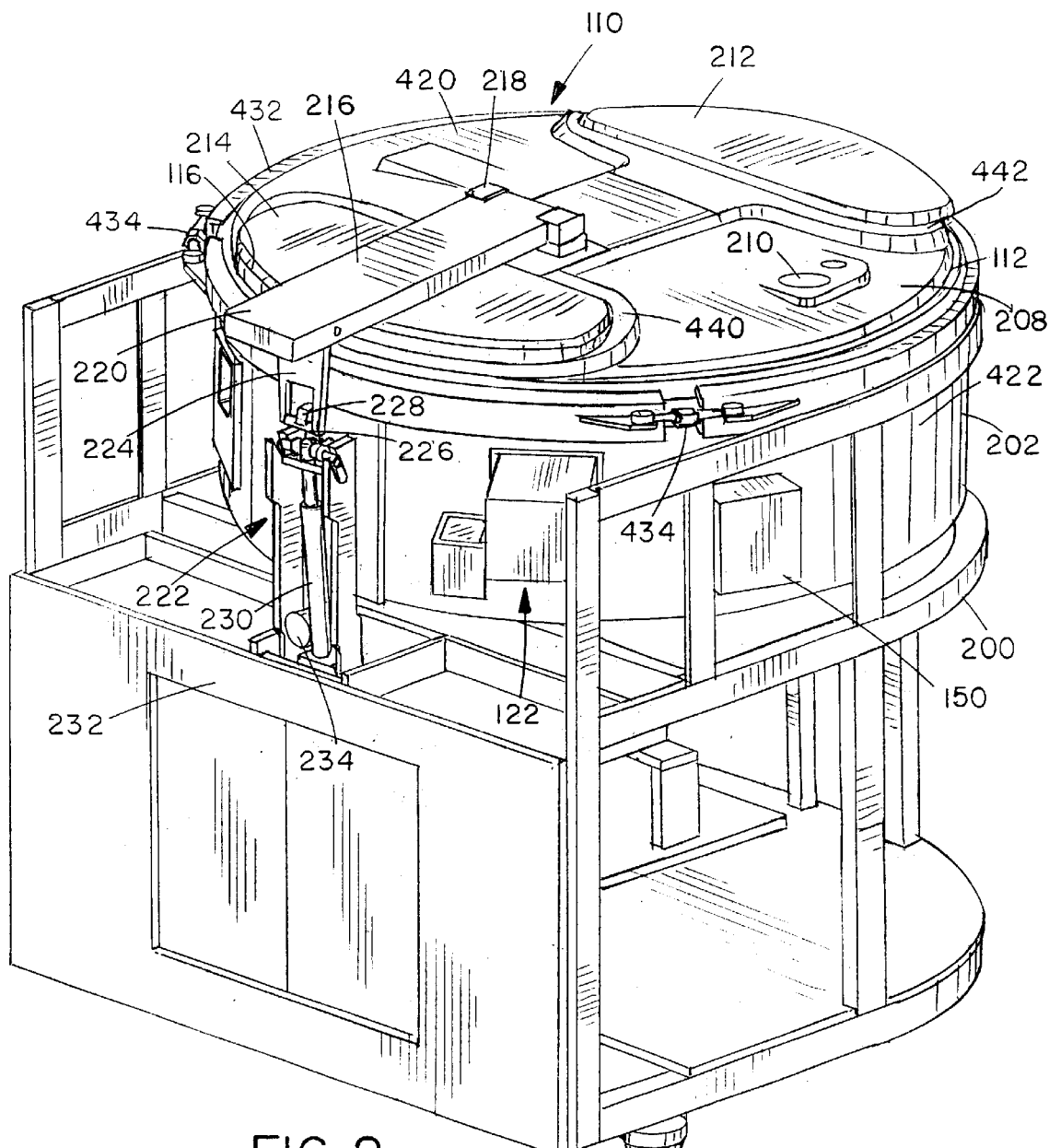
FIG. 2 is a perspective view of the basic system including the centrifuge.

Main Unit 100:

Referring to FIG. 2, centrifuge frame 200 supports the centrifuge 110 and other components of main unit 100. Centrifuge frame 200 may be formed from steel, iron, aluminum or other metal having sufficient strength and stiffness to support the weight of the centrifuge 110 and related equipment. The metal of which frame 200 is formed is preferably coated, painted or otherwise treated to resist corrosion from exposure to harsh chemicals used in the operation of the system. Frame 200 may be fitted with wheels and manual leveling plates to facilitate positioning and movement of the cleavage/evaporation system.

Figure 3:
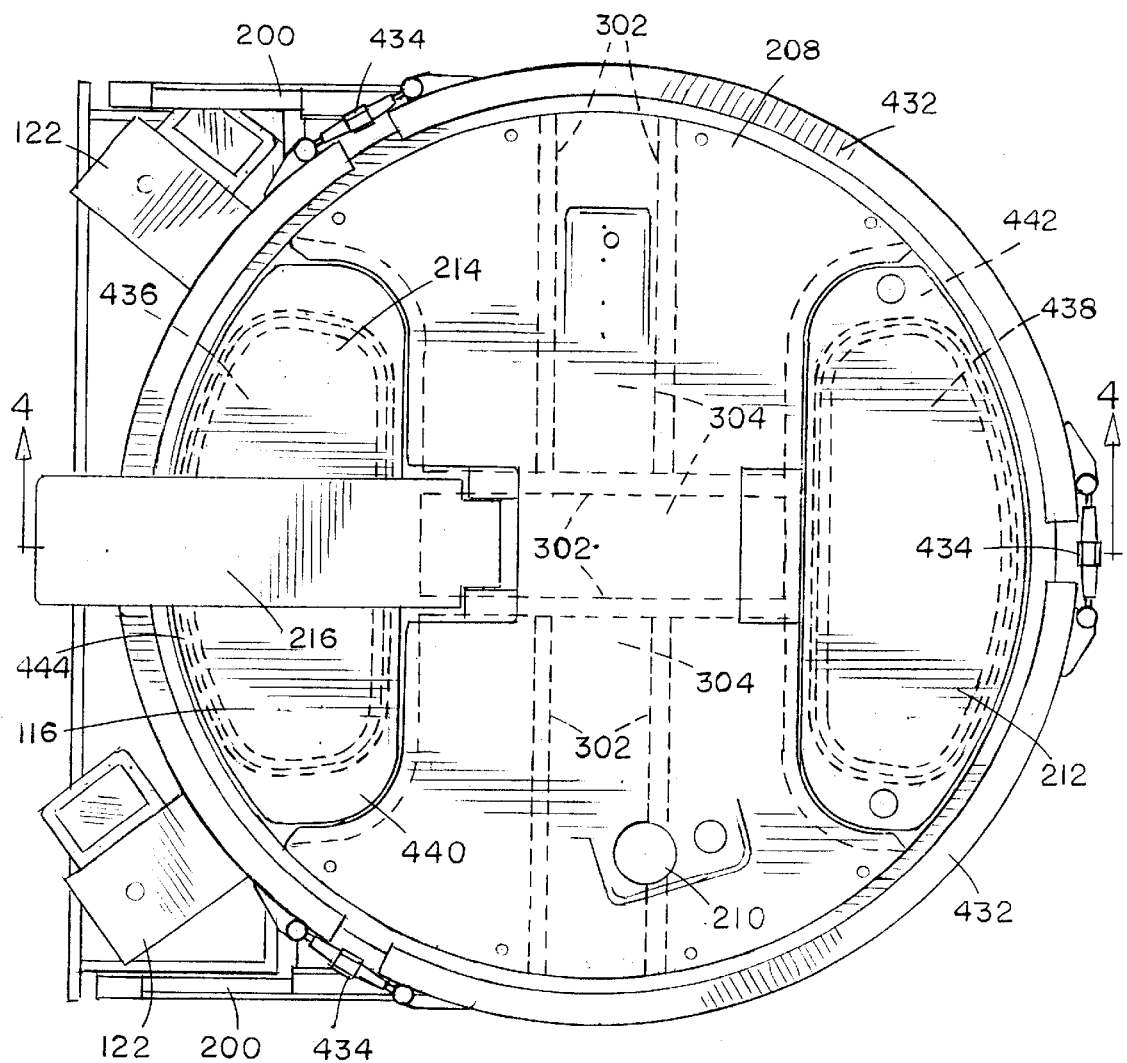
FIG. 3 is a top plan view of the system.

Centrifuge 110:

As shown in FIG. 1, centrifuge 110 comprises chamber 112, stainless steel rotor 114, a software-controlled locking access door 116, drive motor 118, and a drive motor controller 119. Centrifuge chamber 112 is configured as a circular or short cylindrical container comprising a top portion 420 and a bowl portion 422, as shown in FIG. 4. Chamber top portion 420 and bowl portion 422 are preferably made of cast aluminum, which may be anodized, or other material that is resistant to corrosion by cleavage solvents used in the system. The interior surface 426 of chamber top 420 is formed with a generally concave cross-section to reduce the overall chamber volume. In addition, a plurality of ribs 302 are formed in chamber top 420, as shown by dashed lines in FIG. 3. Ribs 302 increase the strength of top 420 while providing recessed areas 304 for installation of certain hardware, such as shown in FIG. 4. When the system is fully assembled, a venting cover 208 is mounted on the top 420, covering recessed areas 304 cover. The venting cover 208 fits closely around the access openings. Venting cover 208 has a plurality of ports formed therethrough. One or more ports 210 provide means for connecting a vent line for drawing vapor from vapor cover 208 to the facility's venting system which may include a blower system and vent lines extending to different areas of the cleavage/evaporation system. One or more second ports may be used to allow a central location for electrical wiring to be fed into other locations. The venting cover is preferably made of polypropylene.

The bottom 424 of bowl portion 422 is formed with somewhat convex profile, with the center sloping upward, to increase strength and decrease chamber volume. Bowl portion 422 has a flange 428 formed around its upper edge with an O-ring seat for retaining an O-ring (not shown) formed therein. The chamber is assembled by aligning lip 430 of top 420 with flange 428 then clamping the lip and flange together using a clamp ring 432 which is tightened by one or more turnbuckles 434 to provide a vacuum-tight seal. Clamp ring 432 is preferably made of anodized aluminum although, generally, fastening hardware used for assembly of the centrifuge chamber and rotor and components attached thereto should preferably be formed of 316 stainless steel for optimal corrosion-resistance.

Chamber top 420 has a front opening 436 and a rear opening 438. Each opening 436, 438 has a raised lip or flange 440, 442 extending around its perimeter which has a flat upper surface with a channel formed therein for retaining a seal ring 444, 446. In order to provide maximum resistance to the corrosive cleavage solvents, seal rings 444, 446 are preferably configured with a TEFLON™ exterior and a flexible, compressible silicone core. In one embodiment, each of seal rings 444, 446 is formed by inserting silicone tubing into TEFLON™ tubing and filling the silicone core with air. In another embodiment, the seal ring is formed by coating a silicone O-ring with TEFLON™.

Referring to FIG. 2, the chamber interior is accessible via rear access door 212 and hinged lid assembly 116, both of which are located on the top surface of chamber top 420. Rear access door 212 is secured over rear opening 438 to chamber top 420 by fastening bolts to provide an airtight seal. Hinged lid assembly 116 comprises a lid body 214 and latching bar 216. Lid body 214 is shaped, to generally fit the outline of front opening 436. Latching bar 216, which is generally rectangular in shape, attaches on its underside to the top surface of lid body 214 and is mounted to chamber top 420 via hinge 218 so that latching bar 216 and lid body 216 can be lifted vertically. As illustrated in FIG. 4, one or more pneumatic struts 450 are pivotally attached at a first end to tabs extending downward from the distal end of latching bar 216 and at a second end to chamber top 240 (within space 304). In the preferred embodiment, a pair of struts 450 is used to absorb some of the weight of the hinged lid assembly 116 to facilitate raising and lowering of the assembly.

The proximal end 220 of latching bar 216 extends radially beyond the outermost extent of centrifuge chamber 202 where it provides a handle for the user to lift the lid assembly 116 and also acts in cooperation with latching mechanism 222. Extending downward from the proximal end 220 of latching bar 216 is a pivotally-mounted fastening latch 224 with lid latch pin 226. Lid latch pin 226 is engaged by hook shank 228 when the hook is extended upward by motor-driven telescoping latching mechanism 230 mounted on top of housing 232 in frame 200. Latching mechanism holds the chamber lid closed during operation of the cleavage/evaporation system.

In the preferred embodiment, control unit 102 includes software for release and locking of lid assembly 116, which is controlled by five inputs and two outputs within the DeviceNet™ control network. The latching mechanism is engaged by the operator lowering the assembly 116 and engaging lid latch pin 226 in hook shank 228. The control unit will detect contact by an input from the "lid-latch-pin-at-shank" sensor. In response, the control unit triggers two output signals: the "lid-latch-motor-engage-direction" output and the "lid-latch-motor-run" output, which cause linear actuator motor 234 attached to latching mechanism 230 to retract the shaft of hook shank 228, pulling the hook down over lid latch pin 226. When lid latch pin 226 enters the hook arm, the "lid-latch-pin-in-arm" sensor is triggered. As the linear actuator continues to pull the shaft of the hook arm 228, lid body 214 is forced against flange 440 to compress seal ring 444 and increase tension in the latching mechanism 230.

Once the tension reaches a specified level, the linear actuator's motor current will increase to the point where the current sensor generates a signal to inform the control unit that lid assembly 116 is fully engaged. The control unit stops linear actuator motor 234 by clearing the "lid-latch-motor-run" output.

Control unit 102 also provides automated release of lid assembly when the cleavage/evaporation process is completed by clearing the "lid-latch-motor-engage-direction" output and triggering the "lid-latch-motor-run" output. This output engages linear actuator motor 234 to extend the shaft of the hook arm 228. When the shaft of the hook arm reaches sufficient extension, the "lid-latch-pin-at-shank" sensor is triggered. The "lid-latch-released" sensor will then be triggered and the control unit will stop the linear actuator motor 234 by clearing the "lid-latch-motor-run" output.

The "lid-latch-over-engaged" sensor generates a signal which can be used to notify an operator that the linear actuator has retracted beyond the point where lid body 214 should have contacted flange 444. This sensor can also be used to notify the operator that the lid latch pin 226 has not properly engaged either the hook shank or the hook arm 228.

Referring to FIG. 11, bowl portion 202 of centrifuge chamber 112 has a plurality of ports 1108 formed in the bottom 1106. Each port 1108 is adapted to receive an infrared-transmissive window 132 which is preferably made of a clear, tempered heat-resistant glass. Each window 132 is secured to bottom 1106 by a mounting frame that fits over the window and is attached by fastening bolts. A TEFLON® gasket (not shown) is placed between the window and the mounting surface on bottom 1106 to ensure a vacuum-tight and corrosion-resistant seal.

A vacuum-access port, indicated by reference numeral 143 in FIG. 1, is formed in the bottom 1106 to provide means for connection of vacuum tubing 145. A vent port 147 can also be formed in the bottom 1106 for attachment to tubing for venting the chamber. A circular opening is formed at the radial center of the chamber to permit centrifuge drive shaft 115 to pass into the interior of the chamber.

A plurality of ports formed in the sidewalls of the chamber bowl portion 202 provide access for the dispensing stations 122 and the bar code reader 150. An imbalance sensor (not shown) can be mounted on the centrifuge body and connected to control unit 102 to shut down the main unit 100 in the event the system becomes imbalanced. PC 104 can display an error message indicating the nature of the error.

Figure 5:
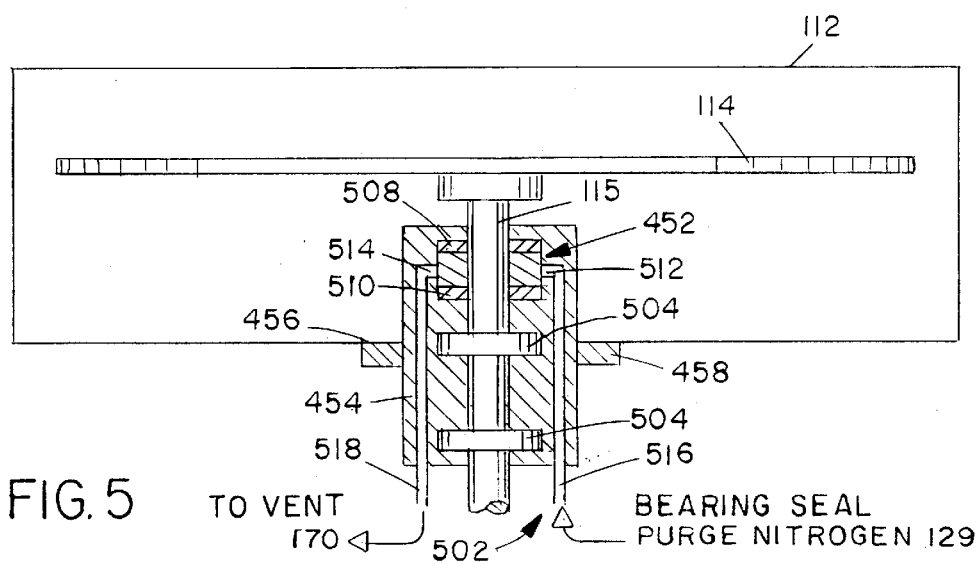
FIG. 5 is a diagram of the bearing purging subsystem.
Figure 6:
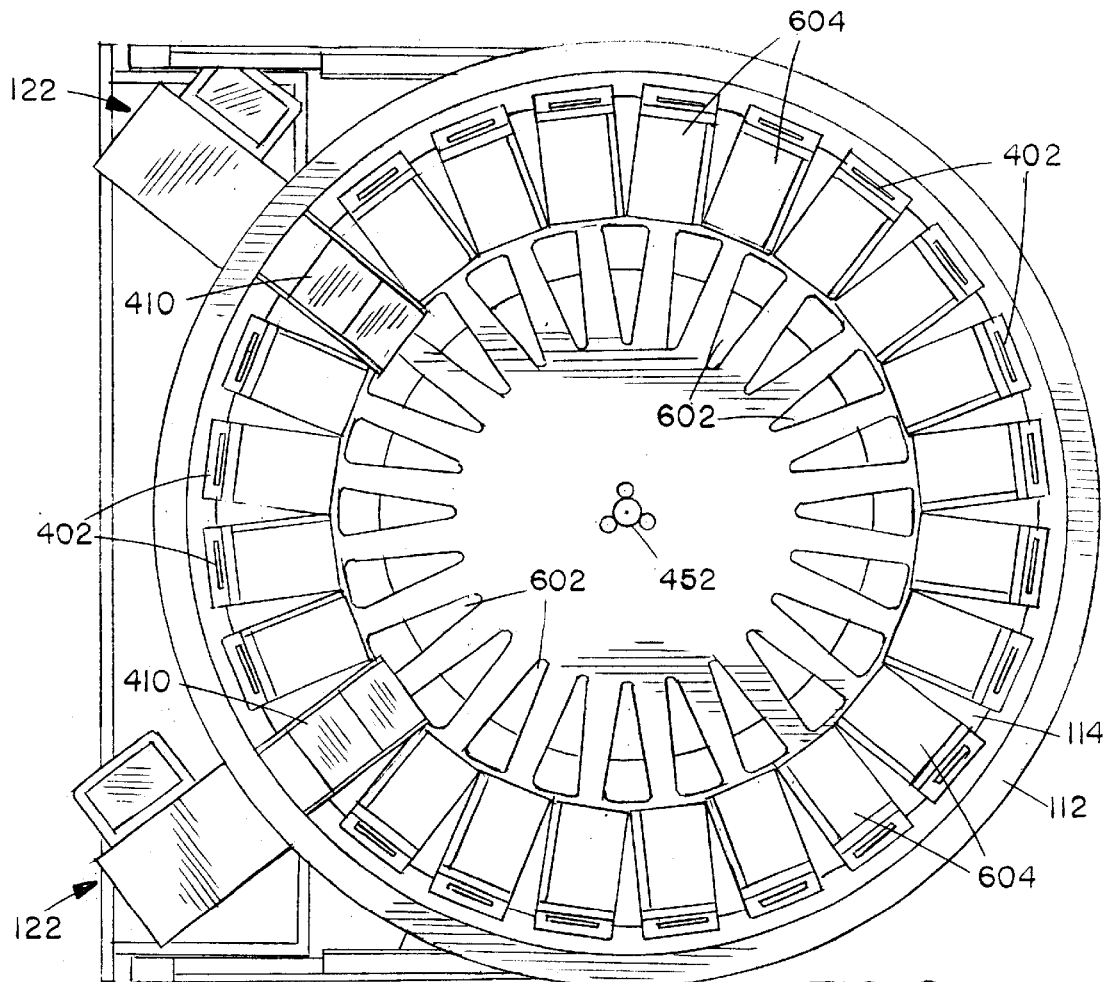
FIG. 6 is a top plan view of the centrifuge with the cover removed.

As illustrated in FIG. 5, rotor 114 is connect to the top of drive shaft 115 which is disposed concentrically with the centrifuge chamber 112. Rotor 114 comprises a circular plate of rigid corrosion-resistant metal, such as 316 stainless steel, with a plurality of openings formed therein, as shown in FIG. 6. A first set of openings 602, each of which are triangular in shape, extend radially inward from a first radius and are distributed radially evenly around rotor 114. These openings are provided to reduce the overall weight of the rotor. The second set of openings 604, which have a rectangular shape, is formed at a second radius outside of the first set of openings. Each of the second set of openings 604 corresponds to a location at which a compound container/collection container assembly 404/406 can be positioned for processing through the cleavage/evaporation system. In the preferred embodiment, there are twenty-four rectangular openings 604 formed in the rotor. Attached to the top surface of rotor 114 at each opening 604 is a support frame 402 which is adapted to retain the container assembly 404/406 during processing.

As shown in more detail in FIG. 7, each support frame 402 has a lower frame portion 706 and a vertical frame portion 708 formed from a corrosion-resistant material such as aluminum or 316 stainless steel. Alternatively, support frame 402 can be a molded or machined plastic or polymer which is corrosion-resistant and sufficiently rigid to prevent deformation of the frame under high speed and/or elevated temperatures. Lower frame portion 706 is disposed at a fixed angle in the range of 15° to 25°, typically on the order of 15°, which causes a larger surface of the fluid in the wells to be exposed for faster evaporation and also reduces the risk of bumping. In an alternative embodiment, the frame can be configured as a swinging bucket which increases its angle by swinging outward at increased rotor speeds. Both frame portions are open to minimize weight and, in the case of lower frame portion 706, to provide an unobstructed path between the heat lamps 138 positioned outside of windows 132 and the bottom of heat plate 704 which is seated in the frame 402 with the container assembly 404/406 on top. Support frames 402 are attached to rotor 114 by mounting tabs (not shown) which extend from the frame for insertion into slots in the rotor and a fastening bolt (not shown) which screws into a threaded bore in rotor 114.

Heat plates 704 are rectangular plates formed from a corrosion-resistant, highly thermally conductive material such as aluminum. A plurality of recesses 710 or shallow wells are formed in the top surface in an array corresponding to the array of wells in collection container 406, so that the bottom of the wells are received within the recesses 710 to enhance distribution of heat around the liquid containing the compound for faster evaporation or the solvent. (For ease of illustration, recesses 710 are shown across only a portion of the upper surface of heat plate 704.)

A bearing ring 452 is located in the interior of the centrifuge chamber 112 and mounts on the drive shaft 115 and over the drive shaft sleeve 454 as shown in FIGS. 4 and 6. The bearing ring 452 is configured as a cylinder with an interior recess. Referring to FIG. 5, the bearing ring 452 has a circulating system 502 which prevents leakage of corrosive substances into the bearings 504. The bearing ring 452 comprises an internal chamber 506 and a plurality of seals 508 and 510. The internal chamber 506 has two openings, a first opening 512 and a second opening 514. The plurality of seals comprises a top seal 508 and a bottom seal 510. The top seal 508 is positioned above the first 512 and second 514 openings while the bottom seal 510 is positioned directly below each opening.

Referring to FIGS. 4 and 5, the drive shaft sleeve 454 is configured as a hollowed cylinder with an outside ring 458 having a plurality of openings for fastening bolts. The drive shaft sleeve 454 will preferably be made of type 316 stainless steel. The drive shaft sleeve 454 mounts on the bottom of the centrifuge chamber 112 and extends through the center opening 456 of the centrifuge chamber 112. The drive shaft sleeve outside ring 458 bolts into the bottom of the centrifuge chamber 112 allowing the drive shaft sleeve 454 to be secured. The drive shaft sleeve 454 has a plurality of sleeve openings 516 and 518 in the interior edges for allowing circulation to the bearing ring circulating system 502. The sleeve openings 516 and 518 extend from the bottom to the top. A plurality of bearings 504 mount inside the drive shaft sleeve 454. The sleeve openings comprise of a first sleeve opening 516 and a second sleeve opening 518.

The first sleeve opening 516 is connected to a gas source 129. The gas source 129 pumps nitrogen up the first sleeve opening 516 and into the first opening 512 of the bearing ring 452. The nitrogen is forced through the internal chamber 506 of the bearing ring 452 because the top 508 and bottom 510 seals allow for the internal chamber to be sealed. The nitrogen is funneled out of the internal chamber 506 to the second opening 514 of the bearing ring 452 and down through the second sleeve opening 518 out to a vent line connected to the ventilation system 170.

Referring to FIG. 1, the drive shaft 115 is configured as a long, cylindrical tube. The drive shaft 115 will preferably be made of a type 316 stainless steel. The drive shaft 115 has a first end 164 and a second end 166. The first end 164 is positioned in the interior of the centrifuge chamber 112 and extends through the drive shaft sleeve 454, through a drive shaft encoder 168, and to the second end 166 which is attached to the center of a drive belt gear 172. The drive belt gear 172 is a flat, circular plate with notches around the outside edges to allow a drive belt 174 to notch into place. The drive belt 174 is attached to a drive motor 118 which is mounted to the centrifuge frame 200.

The drive motor 118 is a servomotor with the ability to operate at different rotational speeds. As the drive motor 118 rotates, the drive belt 174 is engaged causing the drive belt gear 172 to turn. The drive belt gear 172 drives the drive shaft 115 which in turn spins the rotor 114. Selection and incorporation of such a drive motor will be apparent to those of skill in 20 the art.

Referring to FIG. 1, a drive motor controller 119 connects to the drive motor 118 using an interface cable. The drive motor controller 119 connects to a control adapter that connects to the control unit 112. The control unit 112 sends positioning commands to the control adapter that are communicated to the drive motor controller 119. The drive motor controller 119 can send positioning data to the control unit 112 and make positioning adjustments as required by the control unit 112.

The drive shaft encoder 168 is used to track the position of the rotor 114. The drive shaft encoder 168 mounts on the drive shaft 115 with fastening screws. The drive shaft encoder 168 has a graduated disk with a periodic grating of lines and gaps. A second track carries a reference mark. The reference mark defines an absolute reference position on the circular graduation and is permanently assigned to exactly one measuring count. The position value is determined by counting the measuring steps. The drive shaft encoder 168 is connected to the drive motor controller 119. The output signal of the drive shaft encoder 168 is sent to the drive motor controller 119 for determining the rotor 114 positioning. Selection and incorporation of such a drive shaft encoder will be apparent to those of skill in the art.

Container assenbly 404/406:

Sample container 404 and collection container 406, which make up container assembly 404/406, are of a molded, plastic construction. The plastic material used will preferably have a high tensile strength and be heat and chemical resistant.

Figure 17:
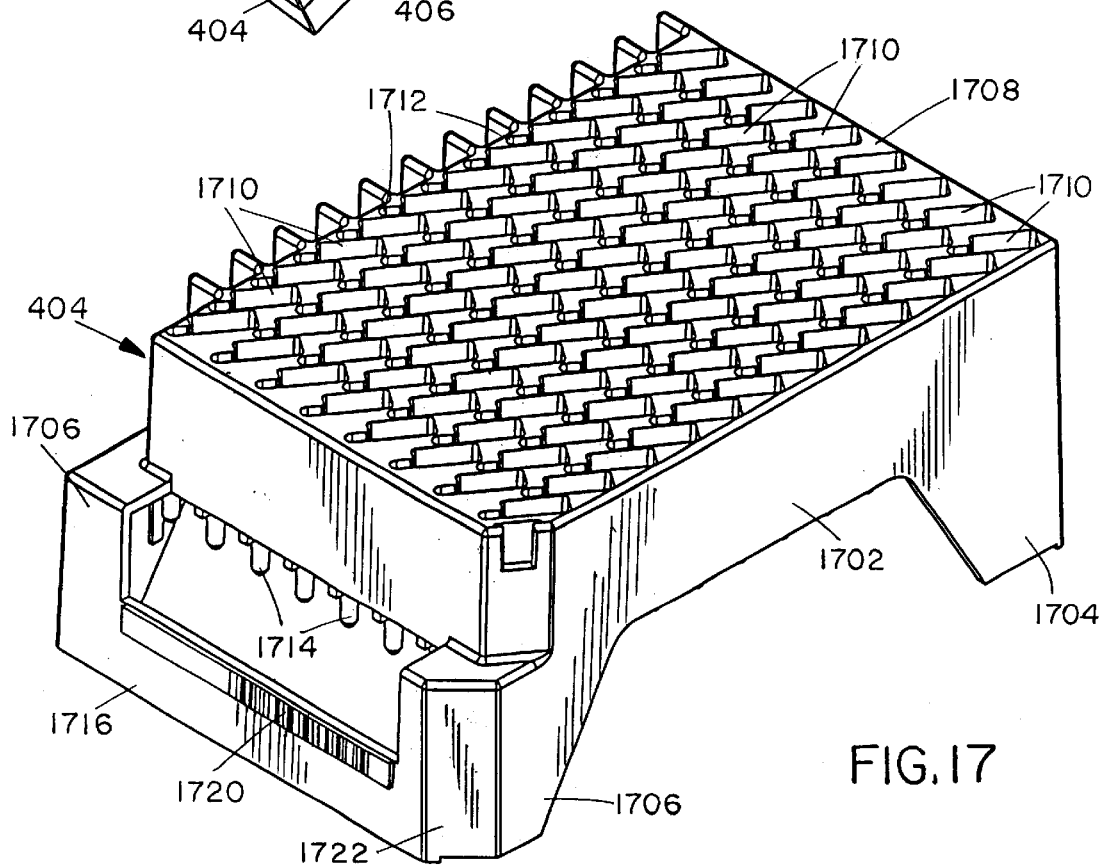
FIG. 17 is a perspective view of the compound container.
Figure 20:
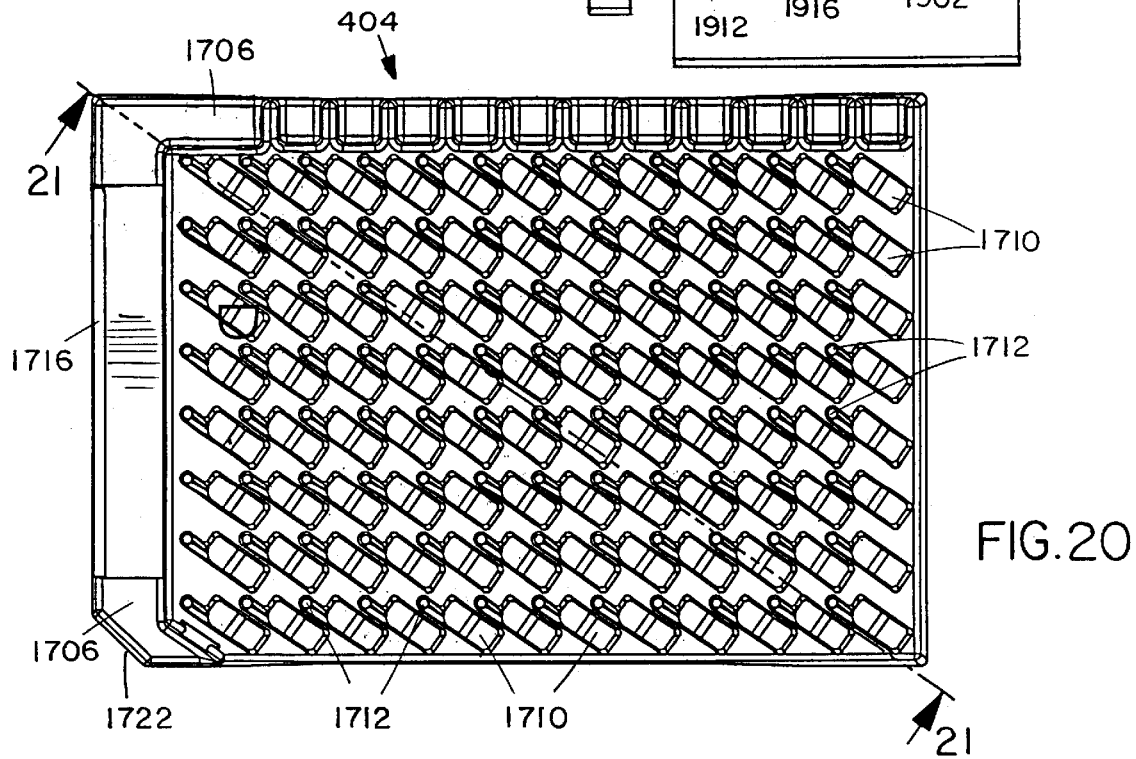
FIG. 20 is a top plan view of the sample container.
Figure 21:
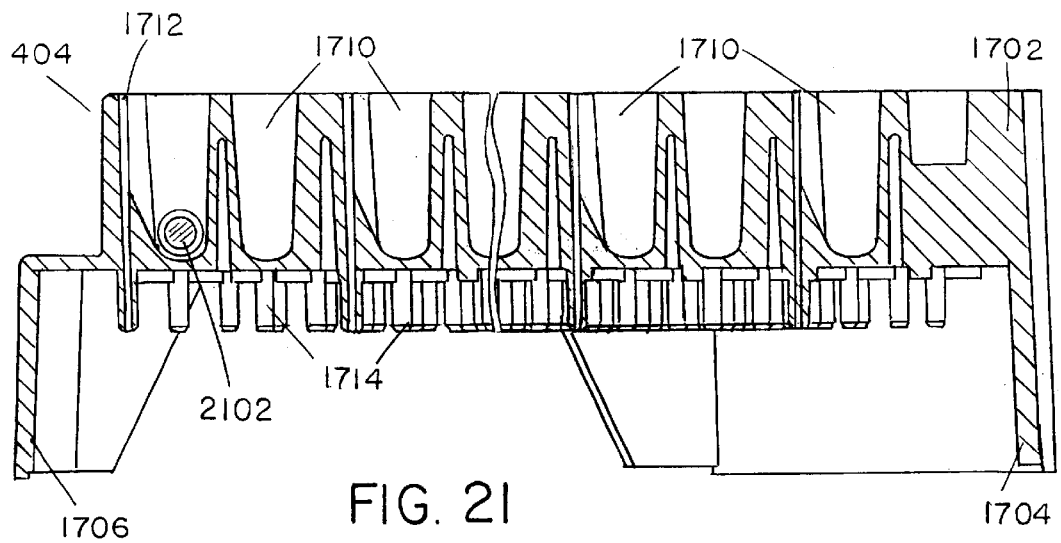
FIG. 21 is an enlarged sectional view taken along line 21—21 of FIG. 20.

As illustrated in FIG. 17, compound container 404 has a generally rectangular body 1702 on top of base extensions 1704, 1706 which act as feet when the container is placed on a flat surface. Rectangular body 1702 has a plurality of wells 1710 extending downward from the top surface 1708. In the preferred embodiment, compound container 404 has 96 wells arranged in an array corresponding to the conventional 96-well format (8 wells×12 wells). The shape of wells 1710 will depend on the configuration of the solid support, and is selected so that the solid support will fall fully down to the bottom of the well in which it placed. In the exemplary embodiment, the solid support comprises a partially porous disk-shaped container with resin inside, which is commercially-available from IRORI (San Diego, Calif.) as the NanoKanTM™. An example of this type of solid support 2102 is shown in the left-most well 1710 of FIG. 21. For this configuration, the compound container's wells 1710 have a rectangular cross-section, as shown in FIGS. 17 and 20, and a U-shaped width with well bottom 2104 slightly larger than the diameter of the solid support 2102, as illustrated in FIG. 21. In another example, where the solid support is one or more spherical beads without a container, the well may have a circular cross-sectional shape dimensioned to receive the spherical bead. A 10 number of other forms of solid supports are known, including tubes, pins, crown, disks, balls, cubes or blocks, and porous containers for retaining particulate material (see, e.g., U.S. Pat. No. 5,961,923.) the wells of sample container 404 can be sized as needed to accept virtually any type of solid support for purposes of the invention.

Figure 25:
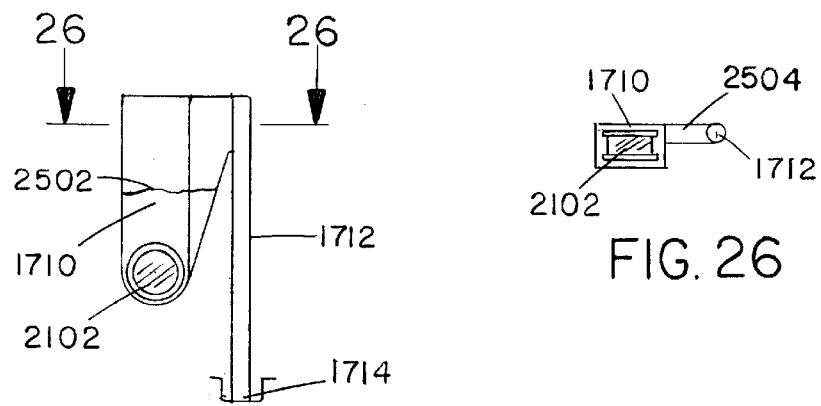
FIG. 25 is a diagrammatic view of a well of a first embodiment of the sample container.
Figure 26:
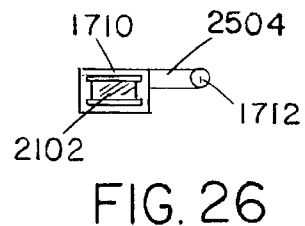
FIG. 26 is a sectional view taken along line 26—26 of FIG. 25.

Further detail of the exemplary embodiment is illustrated in FIGS. 25 and 26, showing the side view of a well 1710 with solid support 2102 in cleaving solution 2502. Bridge portion 2504 slopes upwardly, away from the bottom and may be, as shown, narrower than well 1710, and particularly solid support 2102, so that only solution containing the cleaved compound can pass across bridge portion 2504 and down into drain tube 1712 when the centrifuge is activated as described below. Solid support 2102 is retained in well 1710 due to primarily to the centrifugal force. Therefore, it is not necessary for bridge portion 2504 and drain tube 1712 to be smaller in diameter that the bead or other solid support. It may be desirable to ensure that a small solid support does not accidently become lodged in the drain tube 1712 by placing a frit or filter at the entrance to the drain, near the bridge portion. Drain tube 1712 is essentially a bore extending from the top of compound container 404 through the bottom and downward therefrom to form nozzle 1714, thus providing a fluid transfer pathway from the sample container 1710 out to the corresponding well in the collection container.

Referring again to FIG. 17, base extensions 1706 extend laterally away from body 1702 with a band 1716 extending between base extensions 1706. The lateral extension acts to increase the overall length of compound container 404 so that it fits over the collection container 406, which has the dimensions of a conventional 96-well plate. A bar code 1720 is affixed to or imprinted on band 1716 to permit tracking of the compounds in the compound container. One of the base extensions 1706 has a diagonal portion 1722 formed at its corner to provide an orientation indicator which restricts the orientation of compound container 404 in the centrifuge to one where the bar code 1720 is readily visible through the bar code reader window 152.

Figure 22:
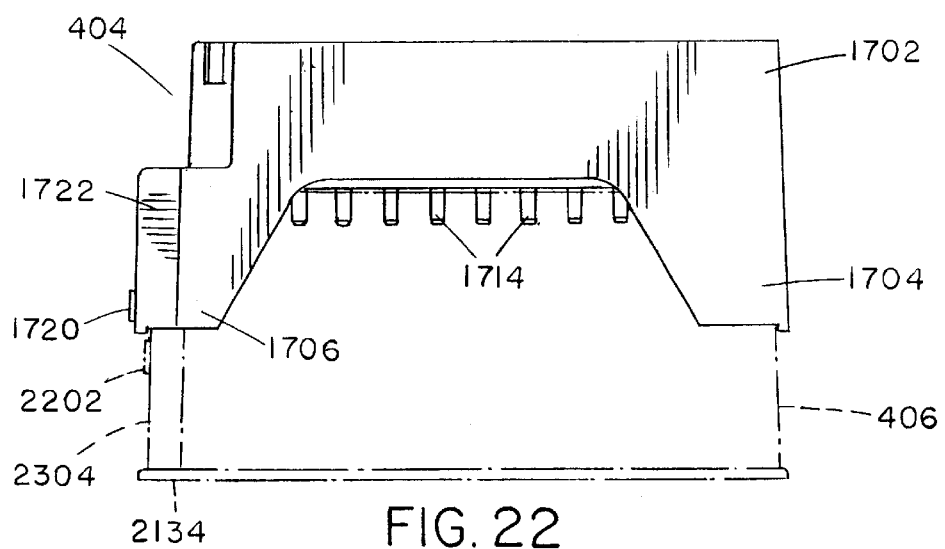
FIG. 22 is a side view of the sample container, with the attached collection container shown in broken line.
Figure 23:
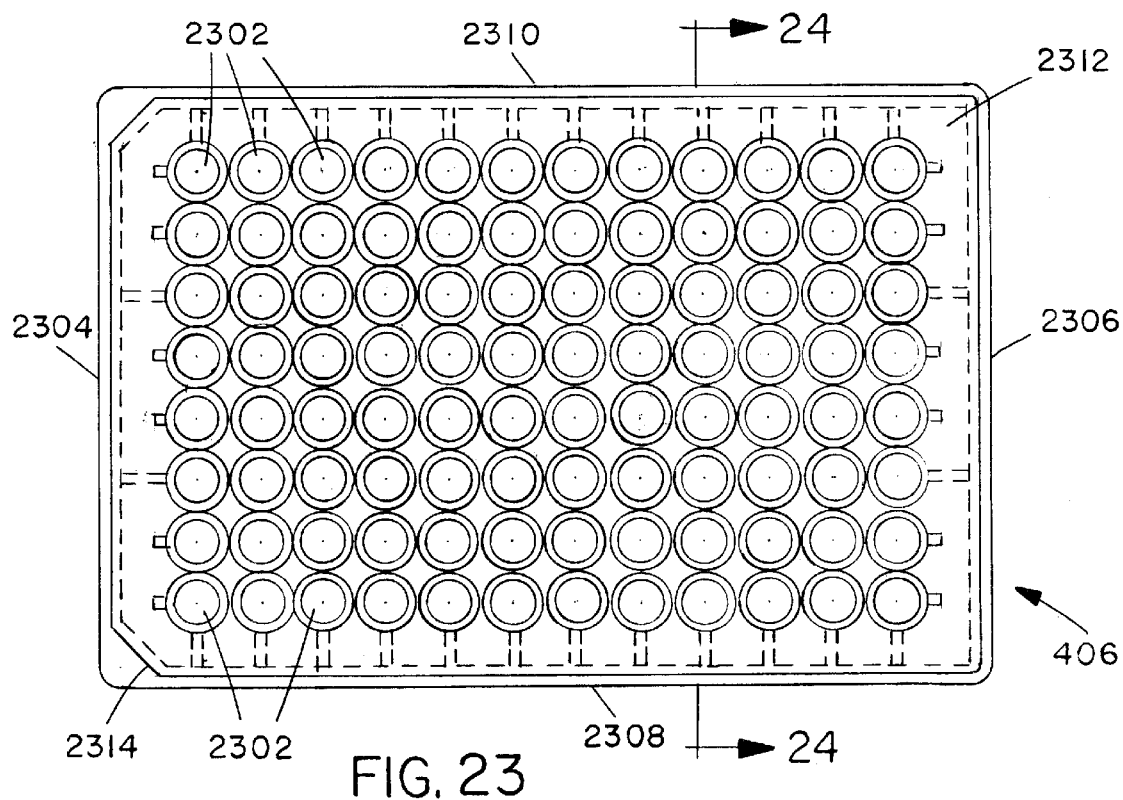
FIG. 23 is a top plan view of the collection container.
Figure 24:
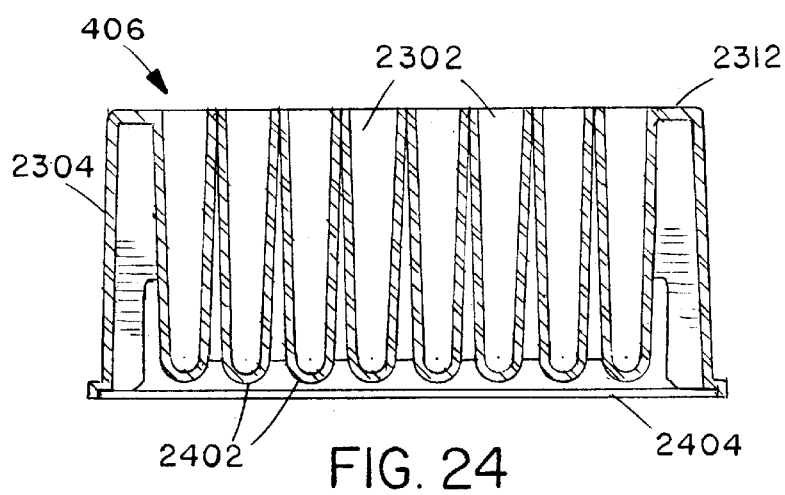
FIG. 24 is a sectional view taken along line 24—24 of FIG. 23.

As illustrated in FIGS. 23 and 24, collection container 406 has a rectangular body with a plurality of cylindrical wells 2302 with rounded bottoms 2402 arranged in an array corresponding to the array of wells 1710 in compound container 404. In the preferred embodiment, collection container 406 is a 96 well plate with an 8×12 array. Positioning and spacing of the wells 2302 closely matches that of nozzles 1714 which extend from the bottom of sample container 404. Wells 2302 extend downward from top surface 2312 into the spacing between sidewalls 2304, 2306, 2308 and 2310. The bottom 2402 of each well is slightly recessed from the bottom edge 2404 of collection container 406. As previously discussed, heat plate 704 has a plurality of recesses 710 formed therein which correspond to the rounded well bottoms 2402, thus providing for more uniform distribution of heat around the outer surface of the well bottoms 2402. In order to provide contact for heat distribution, the separation of sidewalls 2304, 2306, 2308 and 2310, i.e., the inside dimension of collection container 406, must be slightly more that the dimensions of heat plate 704, so that heat plate 704 fits within the container's sidewalls to permit contact with the bottom of collection container 406. The external dimensions of collection container 406 must be slightly smaller that the interior dimensions between base extensions 1704 and 1706, so that the base extensions fit over the corners of collection container 406 to form container assembly 404/406. As best shown in FIG. 22, bar code 2202 is affixed or imprinted on sidewall 2304 at a position below the compound container bar code 1720, so that both bar codes are clearly visible for reading by bar code reader 150. An orientation aligner 2314 comprising a diagonal across one corner of the container ensures that the two containers can be assembled only when they are correctly oriented, which, in turn, ensures that the bar codes 1720 and 2202 are clearly visible for reading.

Sample container 404 is joined to the top of collection container 406 by sliding the base corners 1704 and 1706 over the corners on top of the collection container. The array of nozzles 1714 extending from compound container 404 closely match the array of wells 2302 in collection container 406.

Figure 30:
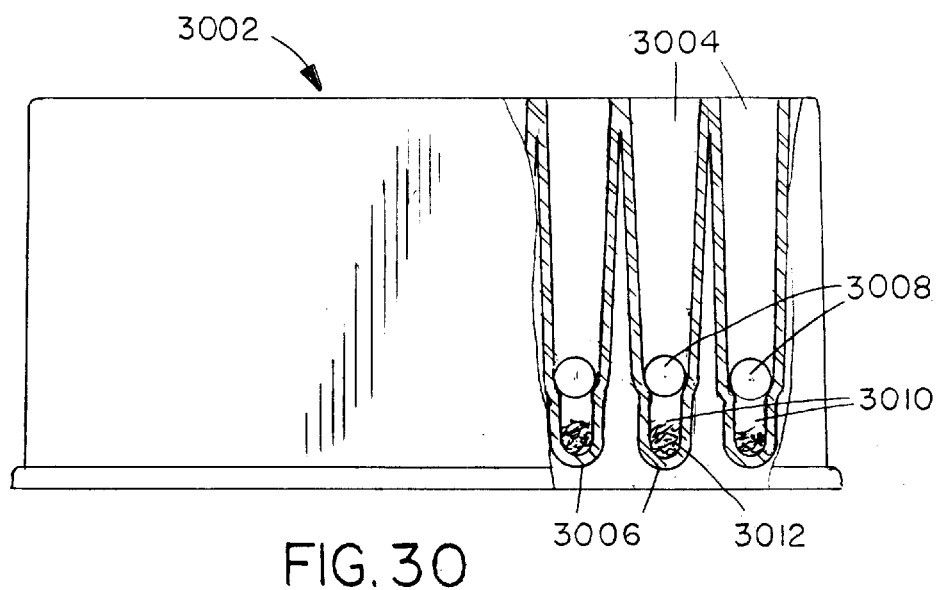
FIG. 30 is a side view, partially cut away, of a transferless sample/collection container assembly.

In an alternative embodiment, the sample and collection container assembly is integrated into one structure, as illustrated in FIG. 30, to form a transferless container assembly 3002. The general configuration of container assembly 3002 is similar to that of collection container 406 in that the wells 3004 are formed as a plurality of closed vessels formed in an array, such as a 96-well plate. The bottoms of wells 3004 are preferably rounded to fit within the recesses in the heat-diffuser plates 710. Container assembly 3002 differs from collection container 406 in that the inner diameter of each well 3004 is reduced at a point part way down the inner volume so that the solid supports 3008 are prevented from falling all the way to the bottom of well 3004. The diameter restriction can be a reduced diameter over-all, as shown, or can be one or more protrusions, such as ribs, ridges, rings or tabs, extending toward the axial center of the well which creates a space smaller than the diameter of solid support 3008 to prevent it from going any deeper into the well. The space below the diameter restriction defines a collection space 3010 into which the cleaved sample can be collected after it is cleaved from the bead 3008. After the evaporation step is performed to remove the solvent, the dried cleaved sample 3012 remains in the bottom of collection space 3010, and container assembly 3002 can be tipped over to remove the solid supports. The dried cleaved sample, which generally has a sticky, viscous consistency, will remain in well 3004 until it is resolubilized or removed using some other appropriate method.

Figure 31:
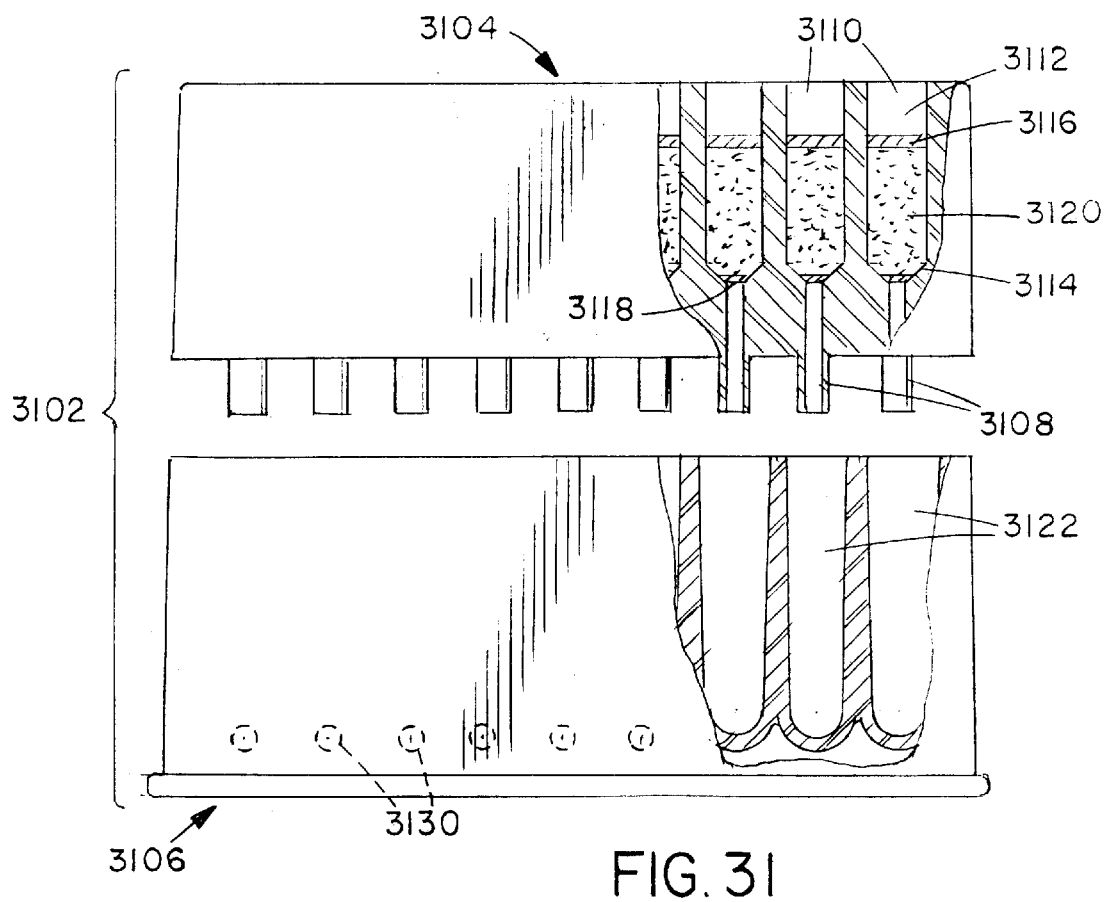
FIG. 31 is an exploded side view, partially cut away, of a sample/collection container assembly for use in DNA purification.

In a second alternate embodiment, the sample/collection container assembly is adapted for use in solid phase DNA purification. As illustrated in FIG. 31, sample/collection container assembly 3102 comprises sample container 3104, waste or collection container 3106.

Sample container 3104 has an array of wells 3110, each of which is essentially a column such as used in column chromatography, i.e., a cylindrical well 3112 which reduces at its lower end to a funnel-like structure 3114 that continues as a narrowed drain tube 3108 extending from the bottom of container 3104. Porous plugs 3116, 3118, formed of porous glass or other appropriate material, are disposed at the top and bottom of the well 3112, respectively, on either side of the solid support 3120, to permit solvent to be introduced at the top and to permit fractionated molecules to pass through and out of sample container 3104 at the bottom.

A second container, waste or collection container 3106 interfits with sample container 3104 and has an array of wells 3122 arranged in a patterns corresponding to wells 3110 and drain tubes 3108 of sample container 3104, so that when the two containers are fitted together, drain tubes 3108 extend into the corresponding well 3122. The washing solutions or eluting agents are introduced using the solvent dispensing system as described. For purification steps, where impurities are removed, the solution carries the impurities through solid supports 3120 and porous plugs 3118 into wells 3122 as a waste solution. In one embodiment of the method, the operator opens the centrifuge chamber after completion of the purification step, removes the container 3106 containing the waste material and replaces it with a clean container 3106 which can be used for cleavage of the DNA from the solid support. In another embodiment, a third container can be used for receiving the waste solution from drains 3108 and directing the solution, using centrifugal force, to a waste reservoir in the centrifuge chamber via generally horizontal channels formed in the container body. Such channel would exit the container body in a direction coincident with the direction of centrifugal force, so that spinning of the container body causes the solution to exit the container. See, for example, the circles 3130 indicated by dashed lines in FIG. 31, which indicate ports which can be connected to a drain manifold leading to a waste collection reservoir within or outside of the centrifuge chamber. In yet another embodiment, the wells of the waste collection container could be configured in a manner similar to sample container 404, with a bridge structure that prevents the solid support and attached DNA from escaping the main well, while the waste solution following a purification step passes over the bridge and out channels connected to a waste collection reservoir.

Gas Suppy Subsystem:

As illustrated in FIG. 1, the gas supply system comprises a nitrogen source 129, a plurality of regulators 182, 183, a pressure sensor 184, and tubing 186. The gas supply system is connected to both dispenser subsystem 120 and to centrifuge chamber 112, providing a purge gas to both subsystems. In the dispenser subsystem 120, nitrogen is used to displace liquid during dispensing. In the centrifuge chamber 112, nitrogen is introduced into the chamber after it is evacuated to provide an inert atmosphere within which the cleavage and evaporation operations are performed. Nitrogen source 129 is a small high pressure cylinder in the preferred embodiment, however other inert gases may be used. Regulator 182, which is manually adjustable, regulates nitrogen source pressure. Regulator 183, also manually adjustable, regulates pressure into the dispenser subsystem 120. Dispense pressure regulator 183 connects via tubing 186 to in-line dispenser displacement valve 185 then into dispenser head 418, and into dispenser bypass valve 187 for routing to centrifuge chamber 112. Each valve 185, 187 is pneumatically controlled by a control adapter in response to a signal generated by control unit 102.

Figure 13:
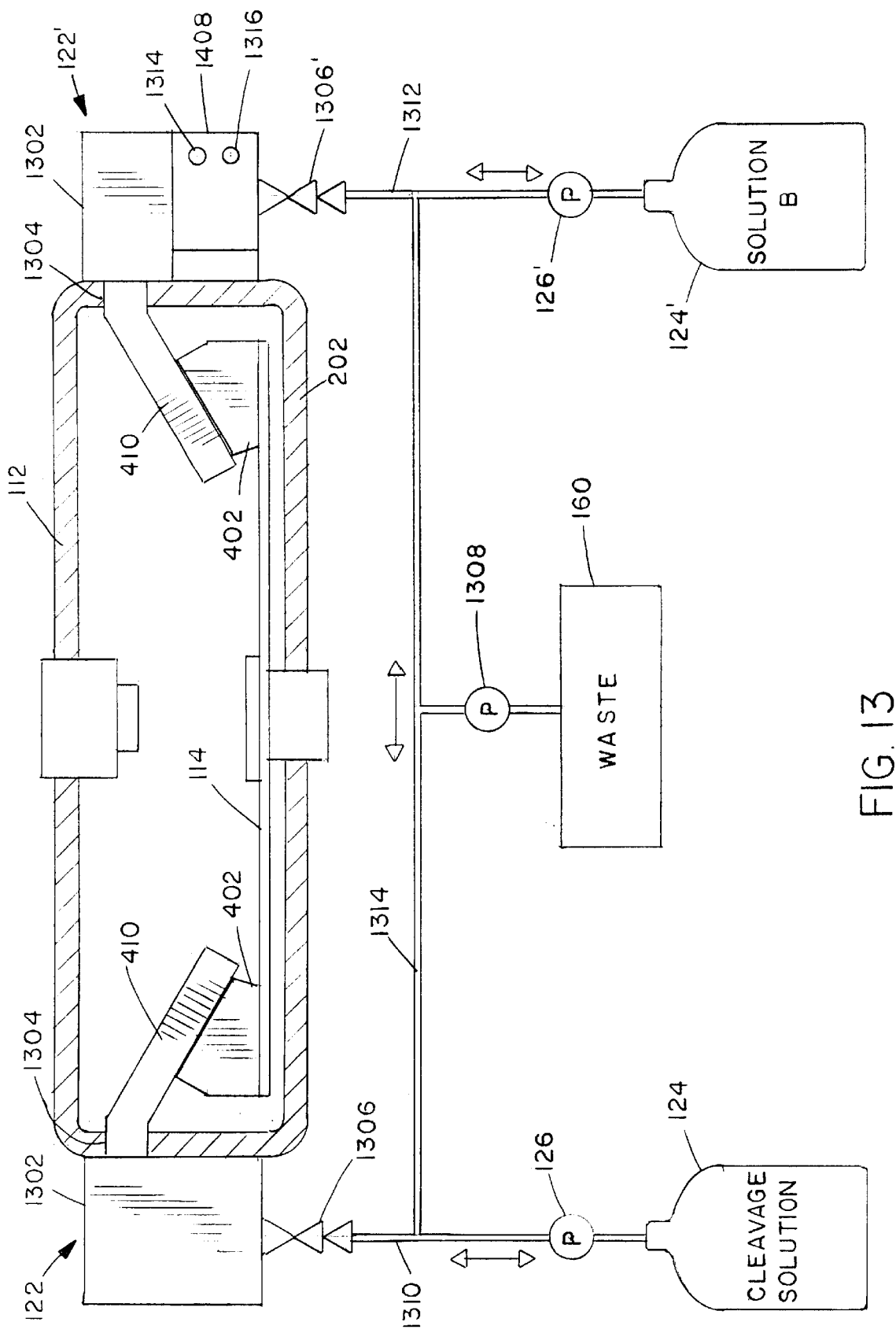
FIG. 13 is a diagram of the solution dispensing subsystem.

Solvent Supply Subsystem 120:

All components of solvent supply subsystem 120 that come in contact with the solvents are made from acid-resistant materials, thus permitting the handling of solvents used in the cleavage of chemical compounds in a sealed chamber, avoiding exposure of personnel to hazardous chemicals and risk of damage to equipment from corrosion. Referring to FIG. 13, in the preferred embodiment, solvent supply subsystem 120 comprises two dispensing stations 122, 122', two source containers 124, 124' and a circulation system for simultaneously filling all wells of a compound container 404 with cleaving solutions.

Figure 14:
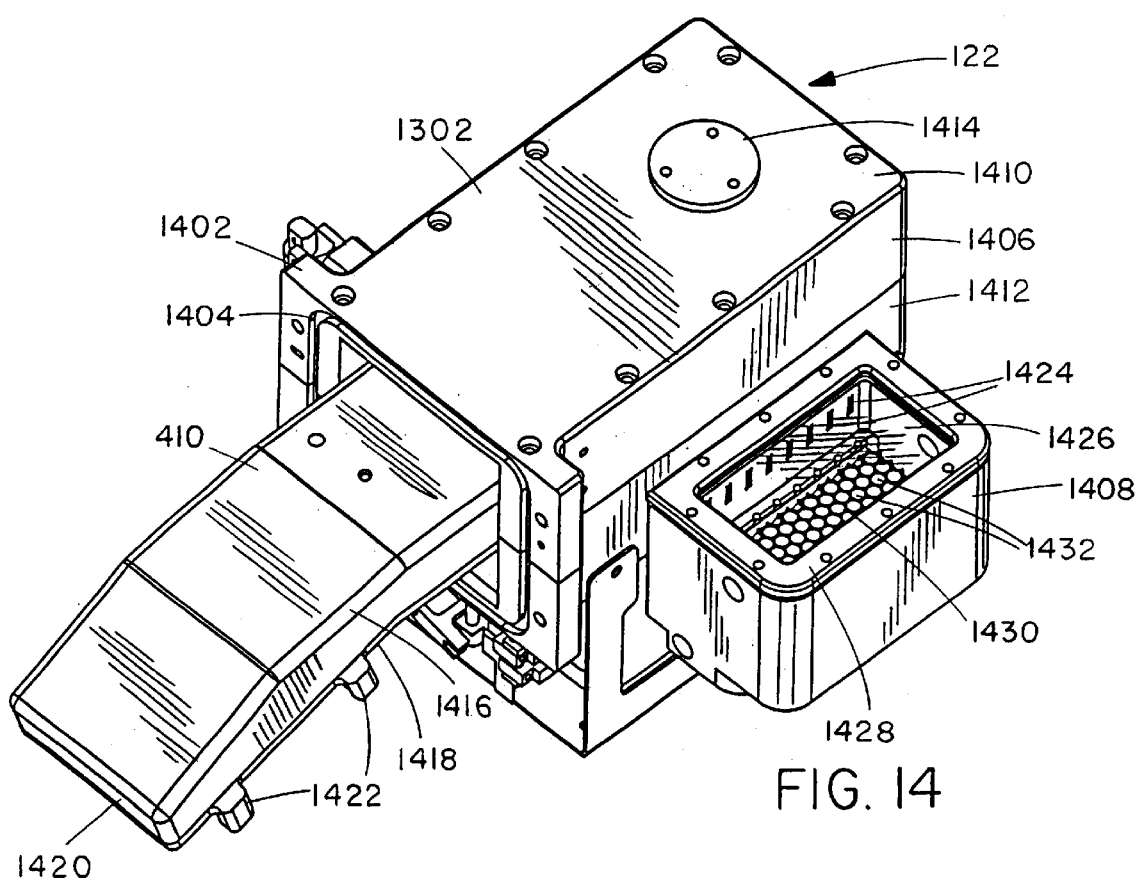
FIG. 14 is a perspective view of a solution dispensing head.
Figure 15:
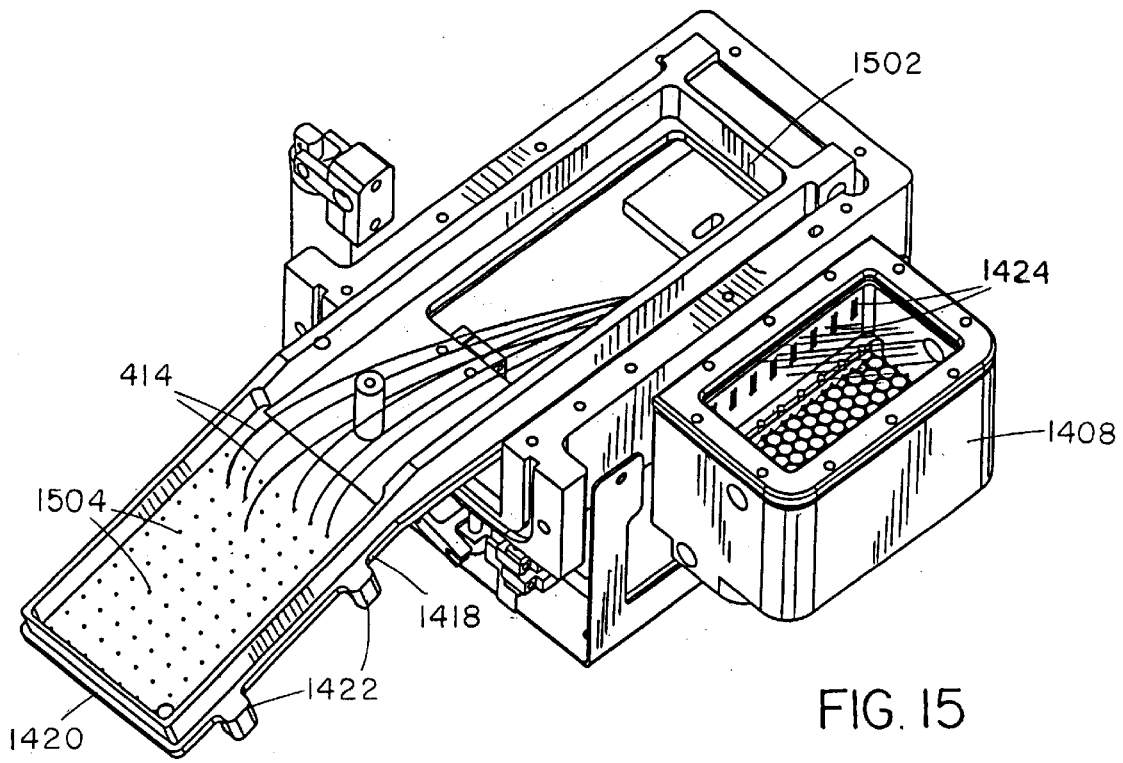
FIG. 15 is a view similar to that of FIG. 14, with the top cover portions removed.
Figure 16:
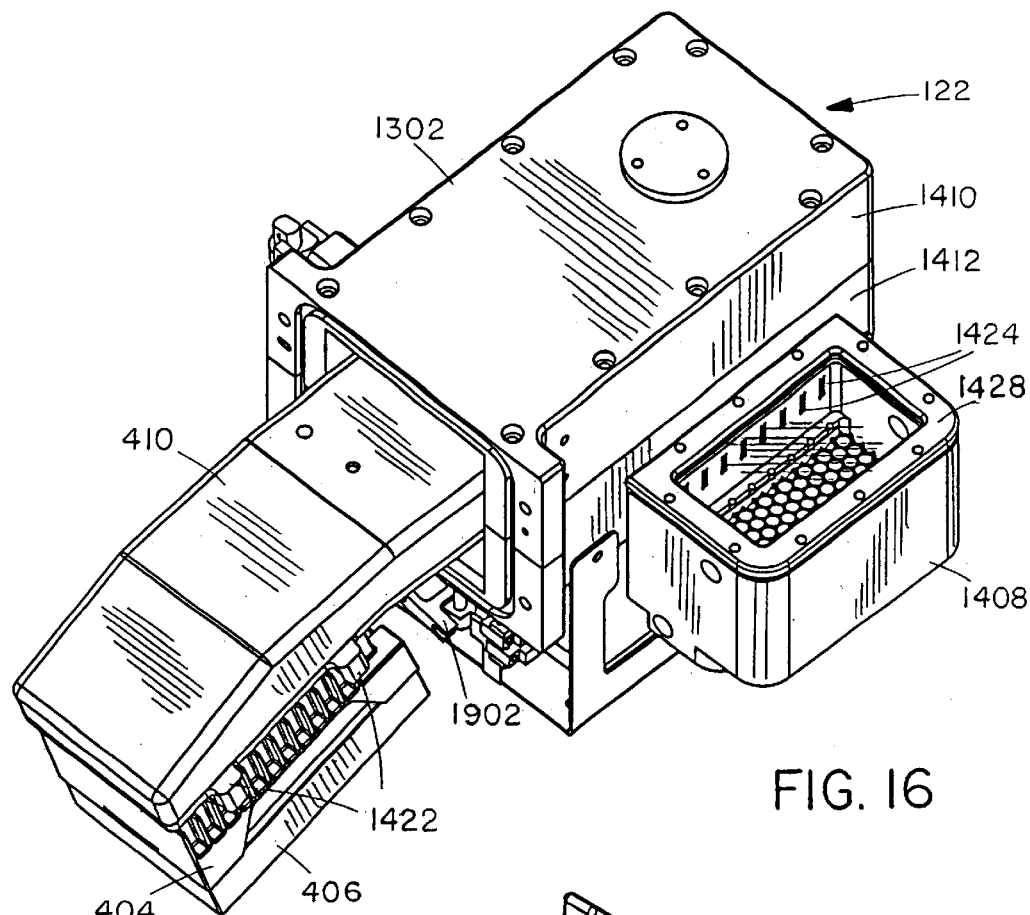
FIG. 16 is a view similar to that of FIG. 14 showing the compound container.

Dispensing stations 122, 122' each comprise an internal portion, consisting of dispensing head 410 and an external portion 1302 which is attached at the exterior sidewall of the chamber bowl portion 202 at ports 1304. Details of each dispensing station 122 are shown in FIGS. 14–16.

Figure 18:
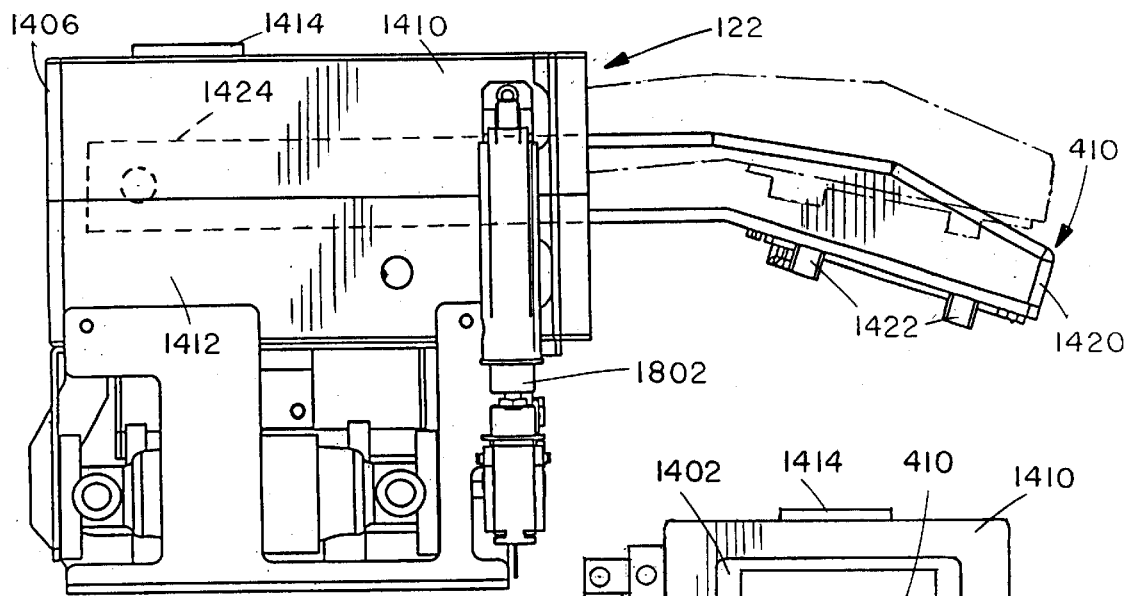
FIG. 18 is a side view of the dispensing unit showing the motion of the head.

Dispensing station 122 comprises a housing 1406, a dispenser head 410, dispensing arm 1902 (shown only in FIGS. 18 and 19) for raising and lowering dispenser head 410, and a reservoir chamber 14,08. Housing 1406 is comprises a top portion 1410 and a bottom portion 1412 which define an interior recess 1502. Top and bottom portions 1410 and 1412 are made of stainless steel and are secured together with fastening bolts. An O-ring or other seal is included when assembling the top and housing to ensure a vacuum-tight seal. Housing 1406 has a flange portion 1402 with a plurality of fastening bores and an O-ring seat 1404 formed therein. A TEFLONO® O-ring is fitted into seat 1404 for providing a corrosion-resistant, vacuum-tight seal between the chamber sidewall and the dispensing station once the mounting bolts (not shown) are tightened. An opening is formed in top portion 1410 which is covered by a removable cover 1414. When cover 1414 is removed, the opening provides access to an adjustment screw the permits a small side-to-side adjustment of the dispenser head 410. Bottom portion 1412 has one or more openings 1424 through its sidewall through which bundles of tubing 414 can pass between the dispensing head 410 and reservoir chamber 1408.

Dispenser head 410 extends from housing 1406 through port 1304 into centrifuge chamber 112 to engage sample containers 404 to confirm proper seating and to fill sample containers 404 with cleaving solution. The proximal end of dispenser head 410 is pivotably mounted within housing 1406 so that it can be raised and lowered. Dispenser head 410 is preferably made of polyvinylidene fluoride (PVDF) and has a top cover 1416 and a bottom portion 1418 which define a hollow body through which a plurality of tubes 414 (shown in FIG. 15) can be fed through openings 1424 to provide fluid transfer from reservoir chamber 1408 to a plurality of dispensing tips 412 extending downward near the distal end 1420 of dispensing head 410. The dispensing tips 412 will preferably be formed from stainless steel tubing to provide sufficient rigidity to provide more accurate positioning. The distal end of each tube 414 is connected to the upper end of each dispensing tip 412 inside of dispenser head 410 and the tips 412 pass through bores 1504 formed through the lower wall of bottom portion 1418. The proximal end of each tube 414 is disposed at or just above the fluid surface level of its corresponding reservoir well 1432. Alternatively, the proximal end of each tube 414 can extend to the bottom of the reservoir well 1432 as long as compensation is made for the well volume that will be taken up by the tubing. It should be noted that for ease of illustration, due to the large number of tubes actually used in the exemplary embodiment, only a small number of tubes 414 is shown in FIG. 15, and the proximal ends or tubes 414 are not shown terminating at a position relative to reservoir wells 1432. It will be readily apparent to one of skill in the art that one reservoir well 1432 corresponds to one tube 414 which corresponds to one bore 1504 and one dispensing tip 412.

Figure 19:
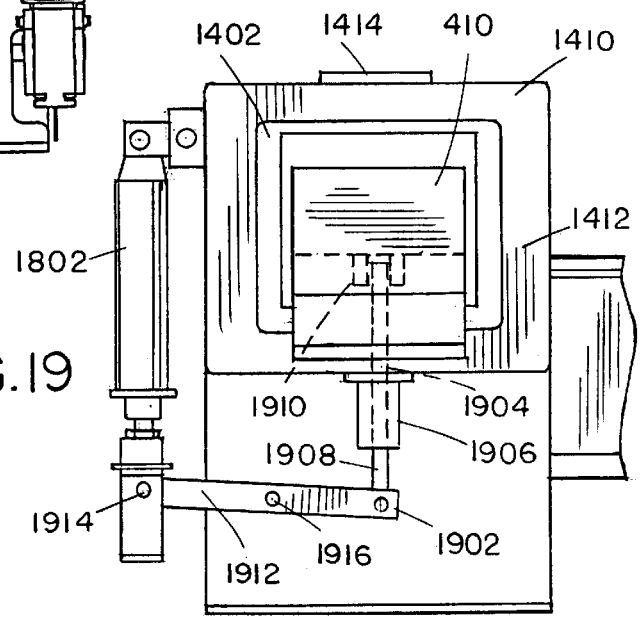
FIG. 19 is a front view of the dispensing unit showing the head actuating mechanism.

Bottom portion 1418 has a plurality of tabs 1422 extending outward and downward from the sides. Tabs 1422 are spaced apart at a distance that closely fits over the top of sample container 404 and are used to secure containers sets 404/406 when dispenser head 410 is lowered. As shown in FIG. 19, dispenser head 410 can be raised and lowered by dispenser arm assembly 1902 which is connected to the underside of the dispenser head. Opening 1904 is formed in housing bottom 1412 permitting dispenser plunger 1908 of dispenser arm assembly 1902 to enter the housing 1410. Dispenser sleeve 1906 is attached to the bottom of bottom portion 1412 to guide dispenser plunger 1908 through opening 1904 and to provide a vacuum seal between dispenser arm assembly 1902 and the housing 1406. Dispenser plunger 1906 attaches at its upper end to the bottom of dispenser head 410 via hinge 1910. The lower end of plunger 1906 pivotably attaches to rocker plate 1912 which, in turn, pivotably attaches to dispenser head actuator 1802 at pivot point 1914. Rocker plate 1912 pivots relative to center pivot 1916.

To lower dispenser head 410, dispenser head actuator 1802 is activated pneumatically to overcome a downward bias provided by a bias spring (not shown) in actuator 1802, lifting the actuator side of rocker plate 1912 and lowering the plunger side. When actuator 1802 is inactive, dispenser head 410 is in the raised position, allowing container assemblies 404/406 to move freely with rotation of rotor 114. Air pressure for activation of actuator 1802 is controlled by opening an actuator valve in response to commands of control unit 102. Dispenser head 410 includes a plurality of sensors for detecting improper mounting of container sets 404/406 or missing container sets on support frames 402. If a container set is discovered to be missing or improperly mounted, the control unit will notify-the operator to correct the problem.

Figure 27:
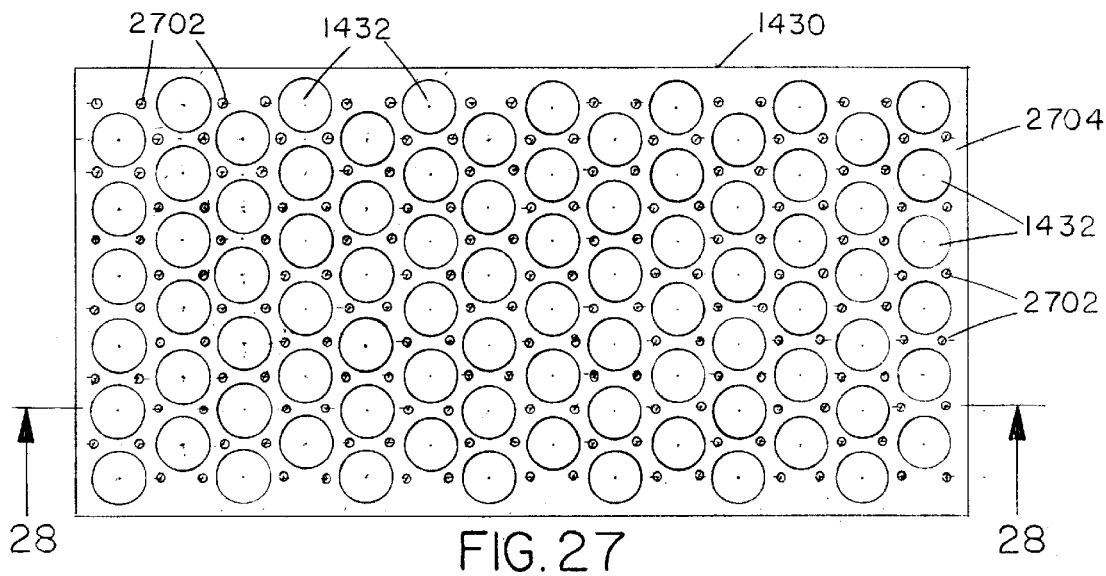
FIG. 27 is a top plan view of the reservoir fill container.
Figure 28:
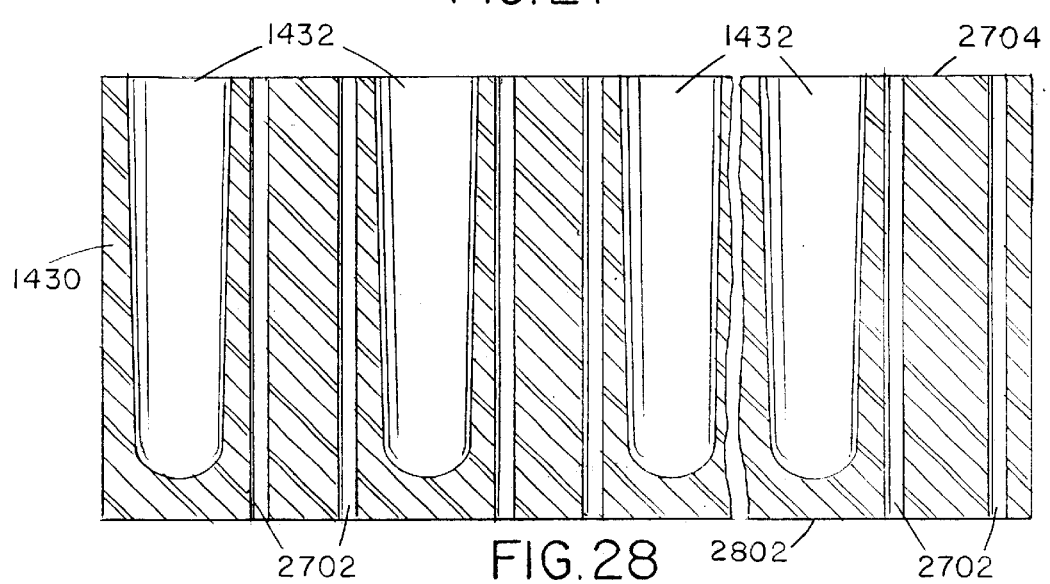
FIG. 28 is a sectional view taken along line 28—28 of FIG. 27.
Figure 29:
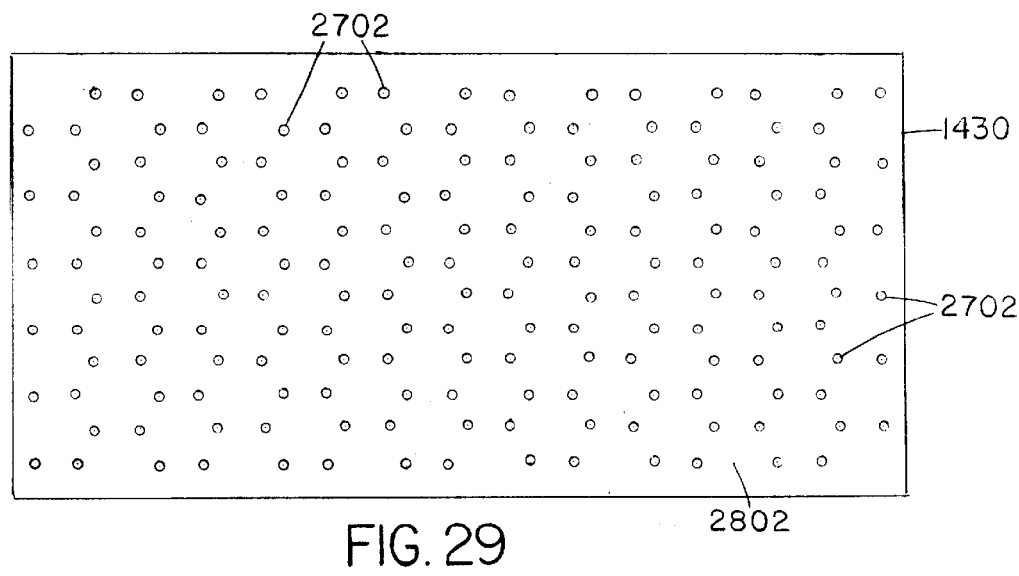
FIG. 29 is a bottom plan view of the reservoir fill container.

Referring to FIG. 14, reservoir chamber 1408 is mounted on the side of the housing 1406. As with the other components of the dispensing station 122, reservoir chamber 1408 must be vacuum-tight. Reservoir chamber 1408 is made of polyvinylidene fluoride (PVDF) to be able to withstand the corrosive solvents used in the system. The top 1426 is glass to permit visual confirmation of the filling operation. Stainless steel frame 1428 is bolted over top 1426 to seal chamber 1408. Fill container 1430 is located inside reservoir chamber 1408 to hold liquid solution and transfer it into tubes 414 for feeding to dispenser head 410. As illustrated in FIGS. 27 and 28, fill container 1430 is a generally rectangular block of TEFLON® with a plurality of solvent. reservoir wells 1432 formed therein, corresponding in number to the number of tubes 414 and the number of wells 1710 and 2302 in compound container 404 and collection container 406, respectively. (It should be noted that for ease of illustration, only a small number of tubes 414 are shown in FIG. 15 while, in fact, there would be one tube corresponding to each reservoir 1432.) Each reservoir well 1432 is surrounded by a plurality of much smaller diameter bores 2702 which extend through the full thickness of the body of fill container 1430, exiting at the bottom 2802 in the pattern shown in FIG. 29. Bores 2702 act as drains to remove excess solvent when reservoir chamber 1408 is filled with liquid to a level above the top of fill container 1430, then drained, causing the liquid to level off precisely at the tops of each reservoir well 1432, even with top surface 2704 of fill container 1430. Excess solvent is returned to source container(s) 124, leaving a measured amount of solvent in each reservoir well 1432. As previously described with respect to FIG. 1, gas supply 129 supplies nitrogen to reservoir chamber 1408 via tubing 186 and dispenser displacement valve 185. The nitrogen increases the pressure within reservoir chamber 1408 creating a pressure differential which causes liquid to be forced through tubing once the reservoir wells 1432 have been filled with the desired amount of solvent.

The liquid. solutions handled in solvent supply subsystem 120 can be corrosive or non-corrosive solutions, for example, trifluoroacetic acid (TFA), dichloromethane (DCM) or dichloroethane (DCE), or a combination thereof, for use in cleavage of synthesized chemical compounds. For biological applications, such as DNA purification, the solvent can be a detergent, typically non-ionic, buffering solution, deionized water, or any eluting reagent appropriate for use in DNA purification as are known in the art. In the exemplary embodiment illustrated in FIG. 13, either solvent source 124 and 124' can be selected to supply one or both dispensing stations 122 and 122'. As shown, dispensing station 122 is connected through first dispenser supply valve 1306 and tubing 1310 to both first source pump 126 and second source pump 126' via a T-connection within tubing 1310. Similarly, dispensing station 122' is connected through second dispenser supply valve 1306' and tubing 1312 to both first and second source pumps 126 and 126' via a T-connection in tubing 1312. Tubing 1314 provides connection between the two dispensing stations 122 and 122' and to the dispenser waste pump 1308 that feeds into waste collection system 160, and specifically into waste reservoir 162. Both source pumps 126 and 126' are reversible, providing flow in both directions. A source spill sensors can be included in cabinets container the source containers for detecting spillage.

Sensors can be included to monitor the filling of each reservoir chamber 1408. In the preferred embodiment, a dispenser overfill sensor 1314 and a dispenser fluid sensor 1316 are used to monitor liquid solution levels in the reservoir chamber. The two sensors attach to a TEFLON® tube (not shown) that connects into reservoir chamber 1408.

During operation, control unit 102 directs centrifuge rotor 114 to increment, placing a container set 404/406 in front of a dispensing station 122. Dispenser head 410 is lowered to confirm that container set 404/406 is properly mounted on support frame 402. If mounting is incorrect, control unit 102 will notify the operator to fix the problem. If correct mounting is confirmed, the dispensing process can begin.

Referring to FIGS. 1 and 13, the solvent supply subsystem 120 system is activated by control unit 102. The system is usually primed before dispensing begins by running a dispensing cycle with no actual dispensing.

Dispenser supply valve 1306 for the first dispensing station 122 is opened while dispenser supply valve 1306' for the second dispensing station 122' is closed. The source pump for the desired solvent (either 126 or 126') is started and liquid solution from the selected. source container 124 or 124' is pumped into reservoir chamber 1408 of the first dispensing station 122. Reservoir chamber 1408 is then filled after which control unit 102 will direct the source pump 126 or 126' to reverse flow, causing the excess liquid solution to drain from reservoir chamber 1408 back into the appropriate source container, thus conserving solvent. Alternatively, after reservoir chamber 1408 is filled, the source pump 126 or 126' is turned off and dispenser waste pump 1308 is turned on so the liquid solution can drain into the waste basin. The waste pump 1308 is only used for the priming process and is not used during actual dispensing. Once completed, the dispenser waste pump 1308 or the source pump 126 or 126' is shut off.

After the priming process has been completed, the same procedure will occur except that once reservoir chamber 1408 has been drained, the reservoirs 1432 in fill container 1430 will be filled with liquid solution. Bores 2702 which surround reservoirs 1432 remove excess solvent when reservoir chamber 1408 is filled with liquid, causing the liquid to level off precisely at the tops of each reservoir well 1432, so that each contains a measured amount of solvent. Excess solvent is returned to source container 124 or 124'. Nitrogen is introduced into chamber 1408 to force the liquid through tubing 414, out the corresponding dispensing tip and into the wells 1710 of compound container 404. This procedure is repeated until all the container sets 404/406 on rotor 114 are filled and the rotor is activated to spin at the appropriate speeds for cleavage and evaporation.

In an exemplary embodiment, the reservoir wells 1432 in each dispensing station 122 or 122' have a different volume, and the same solvent can be dispensed by each station, with a larger volume being dispensed initially by one station 122, and a smaller volume being dispensed by the other station 122' at a later point during the process, to top off wells 1710 during cleavage to compensate for evaporation or other losses of solvent. For example, for cleavage of a chemical compound from a solid support, station 122 would dispense 250 microliters of a 50:50 TCA/DCM mixture at the beginning of the cleavage process, then after incubation for about one hour, station 122' would dispense 100 microliters of the same mixture, after which incubation would resume. After completion of incubation, the samples could be rinsed with methanol by switching to a different source container containing methanol and dispensing methanol via one of dispensing stations 122 or 122'

Temperature Control Subsystem 130:

The temperature control subsystem 130, shown in FIG. 1, provides the ability to independently control and monitor the temperature of the centrifuge 110. In particular, temperature control subsystem 130 addresses the problems that occur when attempting to evaporate a solvent while pulling a vacuum. According to well-known principles of thermodynamics, i.e., PV =RT, under vacuum the temperature drops, resulting in a very slow rate of evaporation of the solvents. In addition, wells in the center of the container arrays will evaporate more slowly because they tend to be cooled by the surrounding wells. Thus, heat input is required to maintain a constant temperature.

Referring to FIGS. 4, 11, and 12, temperature control subsystem 130 comprises a heat/temperature controller 1104/1206, a plurality of heat lamps 138, a plurality of heat plates 704, at least one thermal sensor 1102, a plurality of resistive heaters 1202, and a plurality of temperature sensors 1204. The temperature control subsystem 130 has two main functions: the first is to regulate the temperature of the heat plates 704 to maintain a constant temperature and the second is to regulate the temperature of centrifuge chamber 112.

The heat/temperature controller 1104/1206 comprises a housing which houses a control element, and an interface to the control unit 112. The temperature/heat controller housing is configured as a box which can be attached to the exterior bottom of the centrifuge chamber or mounted within the support frame of the centrifuge assembly. The control element comprises a circuit board with one or more integrated chips (ICs) mounted thereon. A heat/temperature control program, which is stored in one of the control element's ICs, allows the heat/temperature controller 1104/1206 to independently control and manage all components of the temperature control subsystem 130.

Heat/temperature controller 1104/1206 includes an interface for communicating with control unit 102 to continuously report temperature-related information and receive updated temperature directives from the control unit 102. Temperature control subsystem 130 functions by independently controlling and adapting heating operations to maintain a constant temperature during evaporation as determined by control unit 102. Specifically, the control subsystem 130 monitors the amount of heat-input required to maintain the pre-determined temperature of the samples, which is typically at or slightly above room temperature. (Again, it should be noted that since the evaporation is occurring under a vacuum, the temperature in the chamber is much lower than room temperature.) Temperature control is achieved adaptively, preferably by way of a neural network, software for which is maintained in control unit 102, or other similar adaptive software routine, allowing it to rapidly respond to, and even anticipate, temperature changes. Exemplary neural network software is commercially available under the trademarks "ThinksTM™" and "ThinksProTM™", published by Logical Designs Consulting of La Jolla, California. Selection of other appropriate software is within the level of skill in the art. Temperature control subsystem 130, in conjunction with the neural network, monitors the heat input required to increase the temperature of the heat plates while measuring the temperature ramping at the heat plates 704 to determine how soon the target temperature will be reached, then gradually decreases the heat input, thus minimizing temperature overshoot, and applying only the required amount of heat input. By controlling the temperature so precisely to ensure uniform evaporation, it is possible to accurately predict when evaporation will be completed, so that the evaporation step can be automatically shut down. This provides a significant advantage over current practices of estimating completion of evaporation by calculating how long it takes to evaporate a given volume of solvent assuming a constant evaporation rate, then adding a fixed amount of time to compensate for non-uniformity. Such prior art practices often result in overheating and burning of samples, and diminishes overall system throughput by taking more time to complete the evaporation process than may actually be necessary.

As illustrated in FIG. 11, an infrared heat lamp 138 is mounted below each heat-transmissive window 132 in the bottom 1106 of centrifuge chamber 112 with the lamp facing directly towards heat-transmissive window 132. Each heat lamp 138 can be independently turned on and off by heat/temperature controller 1104/1206.

Referring to FIG. 7, heat plates 704 are rectangular plates formed from a corrosion-resistant, highly thermally conductive material such as aluminum. A plurality of recesses 710 or shallow wells are formed in the top surface in an array corresponding to the array of wells in collection container 406 as shown in FIG. 23, so that the bottom of the wells are received within the recesses 710 to enhance distribution of heat around the liquid containing the compound for faster evaporation or the solvent. (For ease of illustration, recesses 710 are shown across only a portion of the upper surface of heat plate 704.)

Referring to FIG. 11, a thermal sensor 1102 is located in a recess formed in the bottom of heat plate 704. Such a sensor can be placed in a single heat plate 704 or a plurality of sensors can be placed in a number of heat plates distributed around the rotor. The thermal sensor 1102 attaches to an electrical wire that connects to an optical (IR) transmitter 135. For protection against corrosion, both thermal sensor 1102 and the electrical wire are encased in TEFLON® tubing. The optical (IR) transmitter 135 has a sealed polyvinylidene fluoride (PVDF) housing and is mounted in the center of rotor 114 by clips. The optical (IR) transmitter 135 is battery powered and has a built in mercury switch. The mercury switch controls battery usage by enabling power to the optical (IR) transmitter 135 only when the rotor 114 is spinning and turns off the power when the rotor 114 is inactive.

An IR-transmissive window 134 is mounted and sealed within top 420 of centrifuge chamber 112, directly above the optical (IR) transmitter 135. A detector 136 is positioned outside of the window for receiving the transmitted signal and converting the infrared signal to an electrical signal which is communicated to the heat/temperature controller 1104/1206.

In one example implementation, the rotor 114 spins container assembly 404/406 mounted on heat plates 704 past each heat-transmissive window132. As the container assembly 404/406 pass each window, the bottom of the heat plates 704 are exposed to the infrared heat lamps 138. As the temperature of heat plates 704 rises, thermal sensor 1102 in contact with one of the heat plates 704 provides a signal indicative of the plate's temperature to the optical (IR) transmitter 135 located below the light-transmissive window 134 in the top of centrifuge chamber 112. Optical transmitter 135 converts the signal to an optical signal which is detected by detector 136 positioned outside of light-transmissive window 134. Detector 136 converts the optical signal to an electrical signal which is communicated to the sample heat controller 1104 to provide feedback for controlling the heat lamps 138.

Referring to FIG. 12, additional heat to the centrifuge chamber 112 is provided by resistive heaters 1202 mounted on the top and bottom of the centrifuge chamber 112. The resistive heaters 1202 will preferably be evenly dispersed to provide uniform heating of the centrifuge chamber 112. The top and bottom resistive heaters 1202 can be independently controlled by the chamber temperature controller 1206. For example, the top resistive heaters 1202 can be engaged while the bottom resistive heaters 1202 are not engaged. One or more temperature sensors 1204 mounted on the outside of the chamber provides feedback to the chamber temperature controller 1206 for controlling the chamber temperature.

A chamber temperature sensor 133, shown in FIG. 1, is included to shut down all temperature control subsystem 130 components if the temperature of the centrifuge chamber 112 exceeds a pre-determined level. The chamber temperature sensor 133 is mounted on the bottom of the centrifuge chamber 112.

Vacuum Subsystem 140:

All components of vacuum subsystem 140 that come in contact with the solvents are made from acid-resistant materials, thus permitting the automated handling of solvents in a sealed chamber, avoiding exposure of personnel to hazardous chemicals and risk of damage to equipment from corrosion. As illustrated in FIG. 1, vacuum subsystem 140 maintains a vacuum within the centrifuge chamber 112, while monitoring and controlling the internal pressure of the centrifuge chamber 112. Vacuum subsystem 140 comprises a vacuum controller 142, a diaphragm pump 146, a Roots blower-type pump 144, a condenser 148, and a plurality of valves 141 and 147.

Vacuum controller 142 controls the operation of the diaphragm pump 146 and is connected to a control adapter, which interfaces with control unit 102. Pressure sensor 194 is connected to vacuum controller 142 to permit monitoring of the pressure in centrifuge chamber 112. Vacuum controller 142 reports pressure information to control unit 102 and receives commands regarding the operation of the pumps, and pressure relief valve 147.

Diaphragm pump 146 compresses vapors pulled directly from the centrifuge chamber 112 or through the Roots blower-type pump 144, depending on the position of pump selector valve 141. The diaphragm pump 146 is used for initial pumping down to a first vacuum level, which, in the exemplary embodiment, is on the order of 50 mbars. In order to protect diaphragm pump 146 against corrosion, all of its components that are exposed to solvent vapor pulled from centrifuge chamber 112 are preferably formed from or coated with TEFLON® or other protective coating.

The condenser 148 is connected downstream from diaphragm pump 146 to condense solvent vapors pumped from centrifuge chamber 112, thus preventing the release of vapors into the atmosphere. Condenser 148 is cooled by water from the recirculating chilled water bath 188, and provides the advantage of not requiring liquid nitrogen such as is required in conventional cold traps. Condensed vapors collected on the coils of condenser 148 are drained into waste reservoir 162, while air entering into the condenser is exhausted via appropriate tubing to the system vent 170. Waste reservoir 162 has a double containment arrangement and includes a waste spill sensor 190 and a waste full sensor 192 to detect spills from the primary container.

Roots blower-type pump 144 is a mechanical pump used for further reducing the pressure in centrifuge chamber 112 once it has been brought down to the first vacuum threshold by diaphragm pump 146. In combination with diaphragm pump 146, Roots blower-type pump 144 can decrease the pressure inside centrifuge chamber 112 to about 1 mbar. When the pump is in use, the exhaust of Roots blower-type pump 144 is connected to diaphragm pump 146 so that the vapors drawn out of centrifuge chamber 112 by pump 144 can be compressed and removed from the exhaust. Roots pump 144 is connected to a control adapter, which interfaces control unit 102. Control unit 102 directly controls all operational aspects of the Roots blower-type pump 144.

The plurality of valves includes a pump selector valve 141 and a chamber pressure relief valve 147. The pump selector valve 141 is connected a control adapter which interfaces with control unit 102. The pump selector valve 141 is an electromechanically-operated ball valve that connects by tubing to Roots blower-type pump 144 and diaphragm pump 146. Control unit 102, communicating via the control adapter, can position the pump selector valve 141 to select pumping by either Roots blower-type pump 144 or diaphragm pump 146.

Chamber pressure relief valve 147 is a spring-loaded valve mounted near the bottom of the centrifuge chamber 112 for emergency release of pressure in centrifuge chamber 112 in the event the pressure exceeds a pre-determined level.

In an example implementation, the control unit 102 will activate pump selector valve 141 to select the appropriate pump depending on which process is to be performed. In the first stage of chamber evacuation, pump selector valve 141 is positioned to direct chamber exhaust to diaphragm pump 146 which compresses the vapors and passes them to the condenser 148 where the vapors are condensed on coils cooled by water from recirculating chilled water bath 188. Any vapors remaining in gas form are exhausted to vapor venting system 170 while the condensed vapors are drained via tubing to waste disposal system 160. Diaphragm pump 146 continues to draw exhaust from chamber 112 until the internal pressure reaches a first vacuum level of about 50 mbar, at which point Roots blower-type pump 144 is engaged.

In the second stage of chamber evacuation, pump selector valve 141 is repositioned to channel the chamber exhaust to Roots blower-type pump 144. Roots blower-type pump 144 reduces the chamber pressure from about 50 mbar to about 1 mbar. The exhaust of Roots blower-type pump 141 is directed to diaphragm pump 146 and to condenser 148 for removal of solvent vapors from the exhaust.

Bar Code Reader 150:

Referring to FIG. 1, the bar code reader 150 is positioned to face the bar code window 152 on the centrifuge chamber 112. The bar code reader 150 is mounted to a pneumatically actuated positioner 154 that provides for the bar code reader 150 to be moved up and down. Air pressure for activation of actuated positioner 154 is controlled by opening an actuator valve in response to commands of control unit 102.

In an exemplary embodiment, rotor 114 positions container assembly 404/406 so that it is in front of bar code window 152 and bar code reader 150 is positioned in the down position. Bar code reader 150 is aligned with collection container bar code 2202 to allow scanning. After scanning has taken place, control unit 102 opens an actuator valve so that the actuated positioner 154 is moved upward to align bar code reader 150 with the compound container bar code 1720. Bar code reader 150 scans the compound container bar code 1720 and the rotor is then initialized by control unit 102 to move to the next container assembly 404/406 into position for reading by bar code reader 150. At this point, bar code reader 150 is in the "up" position and will scan the compound container bar code 1720 of the new container assembly 404/406. Control unit 102 will then close an actuator valve so the actuated positioner 154 will move bar code reader 150 to the "down" position. Bar code reader 150 will repeat the same process until all container assemblies 404/406 are scanned. It will be apparent to those of skill in the art that other positioning schemes may be used to position bar code reader 150 when needed for reading two separate bar codes, which may include the use of optical means such as rotating mirrors, or may utilize two separate bar code readers.

System Operation:

In a first exemplary implementation, sample chemical compounds to be cleaved from their solid supports are placed in a container assembly 404/406 then loaded into the cleavage/evaporation system by opening the hinged lid 116 of the centrifuge 110 and placing the container sets 404/406 and heat plates 704 onto support frames 402 located on top of the rotor 114. The operator may turn the rotor 114 by hand in order to access and load all of the support frames 402 with container sets 404/406 and heat plates 704, or a switch or other control means can be used to incrementally turn the rotor to present the loading stations one at a time. Once all desired support frames 402 are filled, hinged lid 116 is closed and locked into place. It should be noted that not all frames need to be filled, and the only requirement is that the support frames be filled in an arrangement that is balanced on the rotor. Vacuum subsystem 140 is engaged and starts running the diaphragm pump 146 to remove the ambient air, then the gas supply subsystem backfills centrifuge chamber 112 to atmospheric pressure with nitrogen. The chamber heating system remains on while the system is idle and during cleavage to maintain the chamber temperature at a constant temperature, e.g., about 2° C. above room temperature. This ensures that all cleavage is performed at the same temperature, regardless of the environmental conditions or level of usage of the system.

Next, control unit 102 begins to confirm the positioning of container sets 404/406 as well as reading bar codes on both containers. The rotor 114 places a container assembly in front of a dispensing station 122. The dispenser head 410 is lowered to make sure that the container assembly 404/406 is properly mounted on the support frame 402. If mounting is improper, the control unit will notify the operator to fix the problem. As each container set is checked for proper positioning, bar code reader 150 scans each unique bar code on the collection container and the compound container. (Note that for transferless containers, only one bar code need be scanned.)

After positioning of all the container assemblies has been confirmed and the bar codes scanned, the dispensing stations 122 are engaged. The dispensing stations 122 prime the solvent supply system and begin dispensing the liquid solutions. Control unit 102 generates a command to increment rotor 14 to position a container assembly in front of each dispensing station 122. The dispenser head 122 is lowered to engage the appropriate container assembly. Liquid solution is pumped from source containers 124 into reservoir chamber 1408 of dispensing station 122. The liquid solution fills to a level above the top of the fill container in reservoir chamber 1408 and the excess that does not remain in the reservoir wells 1432 is drained back into the source container 124. A measured amount of solvent remains in reservoir wells 1432. In the exemplary embodiment, using a mixture of 50% TCA and 50% DCM, 250 microliters is retained in each reservoir well 1432.

The dispenser bypass valve 187 is closed and dispenser displacement valve 185 is opened by commands from control unit 102. Nitrogen is pumped through dispenser displacement valve 185 into reservoir chamber 1408. As reservoir chamber 1408 is pressurized, the liquid solution in the reservoirs 1432 is forced through tubes 414 and dispensed into the container assembly 404/406 that is positioned under the dispensing head 410. This procedure continues until all of the desired container assemblies are filled with liquid solution.

As is known, during cleavage using solvents such as TFA, a phenomenon known as "creep" can occur, where well vapors can condense on or near the upper surface of the wells in the compound container, and, over time, move from well-to-well, resulting in cross-contamination of compounds contained in the wells. To address this problem, after the container assemblies 404/406 have been filled, rotor 114 is activated to spin the container assemblies at a low rotational speed, e.g., 20–30 r.p.m. The low rotational speed acts in a manner similar to air blowing across the tops of the wells, carrying solvent vapors away from a well before they can condense in other wells.

To provide an example, for procedures using a 50:50 mixture TCA and DCM, after an incubation of about an hour, the rotor will be halted and dispensing station 122' will be used to dispense 100 microliters per well into each container assembly 404/406 to top off each sample well to compensate for solvent that evaporates or is otherwise lost during incubation. After all sample wells have been filled, rotor 114 is again activated to spin at low speed, and incubation continues until cleavage is completed, which will be on the order of a few hours. Selection of appropriate cleavage conditions and duration will depend on the type of samples to be cleaved and the type and concentration of solvent. Those of skill in the art will be capable of selecting appropriate parameters for cleavage using the inventive system and method.

When cleavage is complete, chamber 112 is evacuated and the rotor speed is increased to a high rotational speed to start the transfer and/or evaporation process. Vacuum subsystem 140 is engaged and starts running the diaphragm pump 146. When the internal pressure of the centrifuge chamber 112 reaches about 100 mbar, Roots pump 144 begins to warm up. At about 50 mbar, the control unit 102 switches the pump selector valve 141 to direct exhaust to Roots pump 144. Roots pump 144 is engaged and its exhaust is fed into diaphragm pump 146. Diaphragm pump 146 compresses the vapors and exhausts them to condenser 148 where the vapors. are condensed on coils cooled by water from recirculating chilled water bath 188. The remaining vapors are exhausted to the vapor venting system 170 and the condensate is drained to waste disposal system 160. This process continues until the internal pressure of the centrifuge chamber 112 is equivalent to about 1 mbar.

The rotor speed is increased to a substantially higher speed, preferably on the order of 800 r.p.m. The centrifugal force of the rotor's spinning causes the cleavage solution and cleavage compound to be transferred from the wells 1710 of compound containers 404 into the wells 2302 of collection containers 406. (In processes using the transferless container assembly 3002, no transfer occurs and this step merely serves as part of the concentration/evaporation sequence.) The high rotational speed during evaporation also reduces "bumping". Temperature control subsystem 130 heats the heat plates 704 to keep the samples at a constant temperature and prevent cooling as the solvents evaporate, and the vacuum subsystem 140 continues to operate to maintain the vacuum within chamber 112 as the solvent vapors are released into the chamber atmosphere, thus assisting in evaporation of the solvent. Temperature control subsystem deactivates chamber heaters 1202 since, under vacuum, heating the chamber 112 has little effect.

As the container assemblies 404/406 pass each window 132, the bottoms of heat plates 704 are exposed to the infrared light of the heat lamps 138. As the temperature of heat plates 704 changes, the temperature sensor 1102 detects the temperature of the heat plates and communicates that information to the infrared transmitter 135. The infrared transmitter 135 transmits an infrared signal through window 134 where it is detected by infrared sensor 136 which then relays the temperature information to the heat controller. The temperature controller monitors the heat-input value, i.e., the energy input by heat lamps 138 and the heat plate temperature to maintain the samples at a constant temperature, typically at or slightly below room temperature. As the volatile solvent evaporates, the heat plate temperature decreases due to the cooling effect of the evaporation. The temperature controller responds to this cooling by increasing the heat input to the heat plates. By monitoring the level of heat-input required to maintain the target temperature, it is possible to determine the evaporation rate of the liquid in the wells and accurately detect the end of the evaporation cycle.

When additional heat is no longer required to compensate for the cooling effect of the solvent, the solvent evaporation is complete. This improves the overall system throughput and avoids the risk of overheating the sample compounds.

After the solvent in wells 2302 of the collection container 406 (or in wells 3004 of transferless container assembly 3002) has been completely evaporated, the gas supply subsystem purges centrifuge chamber 112 to remove residual vapors and the rotor drive motor is turned off, allowing the rotor to slow and eventually stop. Control unit 102 then sends a command to unlock the hinged lid 116, allowing the operator to open hinged lid 116 and remove the container assemblies 404/406 from the centrifuge 110. The evaporation cycle where the solvent is TFA or DCM, or a combination of the two, will take on the order of 20 minutes This implementation is only meant to be an example for illustrative purposes.

In a second exemplary implementation, DNA purification is performed by introducing biological samples, e.g., whole blood, plasma, buffy coat, bone marrow, viral or bacterial suspensions, etc., into wells 3110 of sample container 3104 of container assembly 3102. Porous glass plugs 3118 or other appropriate porous material are placed in the lower ends of cylindrical sections 3112 to prevent solid support material, such as resin or silica frit, from escaping through drain tubes 3108. A second porous glass plug 3116 can be placed on top of the solid support to prevent material from escaping at the top of well 3110. Container assembly 3102 is placed on the centrifuge rotor and the centrifuge chamber is closed. In an alternate implementation, the column arrangement can be replaced by using a solid support such as that illustrated in FIG. 21, i.e., a porous container filled with an appropriate solid support material such as resin or silica frit, for example, the IRORI NanoKanTM™ or IRORI MicroKan®. In this latter embodiment, the sample/collection container assembly described and shown in FIGS. 17 and 21–25 can be used for processing of biological samples.

The centrifuge chamber can be evacuated and backfilled to atmosphere with nitrogen to ensure uniform processing conditions. Purification solution, e.g., a detergent-containing buffer, is introduced by positioning each container assembly 3102 under a dispensing station. After each container assembly has received the appropriate amount of solution, the rotor activated and, where appropriate, the temperature increased. It may be possible to perform multiple washing steps or other purification steps within a centrifuge cycle by introducing a second solution or a plurality of second solutions into the container wells. The waste solution is collected in the wells of waste collection container 3106. After one or more purification steps is completed, the centrifuge rotor is stopped, the chamber brought back up to atmosphere, and the operator opens the chamber door to access the sample containers. The waste collection container 3106 is removed from each assembly 3102 and a clean collection container is assembled with the sample container 3104. The assembly is then placed back on the rotor, the chamber evacuated and backfilled, if desired, and elution reagent is dispensed into each of the container well by one of the dispensing stations. The chamber can be heated to incubate the samples while centrifugation assists in cleaving the DNA samples from the solid supports. The remaining steps are similar to those described above for the chemical cleavage and can be readily adapted by one of skill in the art to complete the purification and cleavage of the biological samples.

The cleavage/evaporation/collection system and the method of using that system provide many advantages over devices and methods currently in use. In particular, the invention provides a highly automated system and method for sequentially washing, cleaving, eluting, concentrating, purifying, and/or collecting a large number of chemical compounds or biological samples in a rapid and cost effective which minimizes the handling of both the samples themselves and the hazardous chemicals used in cleavage or other processes. The system is sealed and constructed of materials that are resistant to the corrosive solvents typically used in cleavage and purification procedures, providing increased safety, higher throughput and better control compared to known systems and methods.

It will be apparent to those skilled in the art that various modifications and variations may be made in the apparatus and process of the present invention without departing from the spirit or scope of the invention. Thus, it is intended that the present invention cover the modification and variations of this invention provided they come within the scope of the appended claims and their equivalents.

We claim:

1. In an automated system for treatment of a plurality of chemical or biological samples, a dispenser for dispensing a treatment solution into a plurality of wells in a multi-well plate, wherein the multi-well plate is disposed within a chamber, the dispenser comprising:

a housing attached to the chamber;
 a dispensing head extending from the housing into the chamber, the dispensing head having a plurality of dispensing tips extending therefrom and arrayed in a pattern corresponding to an array of wells in the multi-well plate;
 a plurality of reservoir wells for retaining a measured amount of treatment solution wherein the plurality of reservoir wells is disposed within a fill container and the housing attached to a reservoir chamber for retaining the fill container, and wherein each reservoir well is surrounded by a plurality of bores extending through the fill container;
 a plurality of tubes extending through the housing and the dispensing head, each tube having a first end and a second end, one tube corresponding to each reservoir of the plurality of reservoirs, the first end being disposed adjacent the reservoir well and the second end connected to a corresponding tip of the plurality of tips; and
 a pressure source for forcing treatment solution from the reservoir wells through the tubes and out of the corresponding tip into a corresponding well of the multi-well plates.

2. The automated system of claim 1, wherein the samples are synthesized chemical compounds and the treatment solution is trifluoroacetic acid (TFA).

3. The automated system of claim 1, wherein the samples are synthesized chemical compounds and the treatment solution is dichloromethane (DCM).

4. The automated system of claim 1, wherein the samples are biological samples and the treatment solution is selected from the group consisting of a detergent, buffering solution, deionized water, and eluting reagent.

5. The automated system of claim 1, further comprising means for raising and lowering the dispensing head to fill the wells of the multi-well plate.

6. The automated system of claim 5, further comprising an alignment device for aligning the wells of the multi-well plate with the plurality of tips.

7. The automated system of claim 6, further comprising an alignment sensor for detecting misalignment.

8. The automated system of claim 1, wherein the housing forms a vacuum-tight seal with the chamber.

9. The automated system of claim 1, wherein the fill container comprises a polytetrafluroethylene block.

10. The automated system of claim 1, wherein the reservoir chamber has tubing connected thereto for supplying treatment solution from a source and for draining excess treatment solution back to the source.

11. The automated system of claim 1, wherein the pressure source comprises a nitrogen source and tubing for connecting the nitrogen source to the housing.

* * * * *